US009402766B2

(12) United States Patent
Akahoshi et al.

(10) Patent No.: US 9,402,766 B2
(45) Date of Patent: *Aug. 2, 2016

(54) APPARATUS AND METHOD FOR PHACOEMULSIFICATION

(75) Inventors: Takayuki Akahoshi, Tokyo (JP); Ravi Nallakrishnan, Westmont, IL (US)

(73) Assignee: Art, Limited, Grand Cayman (KY)

( * ) Notice: Subject to any disclaimer, the term of this patent is extended or adjusted under 35 U.S.C. 154(b) by 30 days.

This patent is subject to a terminal disclaimer.

(21) Appl. No.: 12/893,874

(22) Filed: Sep. 29, 2010

(65) Prior Publication Data

US 2015/0335482 A1  Nov. 26, 2015

Related U.S. Application Data

(63) Continuation-in-part of application No. 12/263,315, filed on Oct. 31, 2008, now Pat. No. 9,132,033.

(60) Provisional application No. 60/984,375, filed on Nov. 1, 2007, provisional application No. 61/246,864, filed on Sep. 29, 2009.

(51) Int. Cl.
*A61F 9/007* (2006.01)
*A61M 1/00* (2006.01)
(Continued)

(52) U.S. Cl.
CPC ......... *A61F 9/00763* (2013.01); *A61B 17/3417* (2013.01); *A61F 9/00745* (2013.01);
(Continued)

(58) Field of Classification Search
CPC ....... A61B 2017/320072; A61B 2017/320096; A61B 2017/320088; A61B 17/3417; A61B 2017/3456; A61B 2217/005; A61F 9/00745; A61F 9/00763; A61M 1/0039

USPC ........... 606/107, 169, 171; 604/22, 264, 118, 604/119, 35
See application file for complete search history.

(56) References Cited

U.S. PATENT DOCUMENTS 4,961,424 A * 10/1990 Kubota ............ A61B 17/22012
601/2
5,478,328 A * 12/1995 Silverman ............... A61M 5/32
604/110
(Continued)

OTHER PUBLICATIONS

Quality 101, Get a Handle on Waviness, Eiji Okada and BNP Media Staff published Apr. 29, 2009, pp. 1-4.
(Continued)

*Primary Examiner* — Bhisma Mehta
*Assistant Examiner* — Jenna Zhang
(74) *Attorney, Agent, or Firm* — Wood, Phillips, Katz, Clark & Mortimer

(57) ABSTRACT

Phacoemulsification needles are configured to cause eccentric or wobble-type motion by being formed to distribute the mass of the needle non-uniformly. In one version the non-uniform property is created by angling the needle's aspiration passage with respect to the needle axis. In another, the needle tip walls are formed with non-uniform thicknesses, with or without including an off-axis configuration with respect to the needle aspiration passageway. In another, the needle tip walls are formed in a scalloped configuration. In another, external protuberances or "bumps" are formed on the needle tip exterior wall surfaces. In another, the needle tip walls have weighted inserts placed therein. In another, the needle tip is formed with skewed bevels and ridges. In another, the needle body is formed with non-uniformly shaped segments. In another, a portion of the needle tip is twisted with respect to the rest of the tip.

12 Claims, 26 Drawing Sheets

(51) Int. Cl.
*A61B 17/34* (2006.01)
*A61B 17/32* (2006.01)

(52) U.S. Cl.
CPC .. *A61M1/0039* (2013.01); *A61B 2017/320072* (2013.01); *A61B 2017/320096* (2013.01); *A61B 2017/3456* (2013.01); *A61B 2217/005* (2013.01)

(56) References Cited

U.S. PATENT DOCUMENTS

| | | | |
|---|---|---|---|
| 5,645,530 A | 7/1997 | Boukhny | |
| 5,676,649 A * | 10/1997 | Boukhny | A61F 9/00745 604/22 |
| 5,725,495 A * | 3/1998 | Strukel | A61M 1/0035 604/22 |
| 5,743,871 A * | 4/1998 | Strukel | A61M 1/0035 604/22 |
| 5,879,356 A | 3/1999 | Geuder | |
| 6,007,513 A * | 12/1999 | Anis | A61F 9/00763 604/22 |
| 6,007,555 A * | 12/1999 | Devine | A61F 9/00745 604/22 |
| 6,165,150 A * | 12/2000 | Banko | B06B 3/00 604/22 |
| 6,402,769 B1 * | 6/2002 | Boukhny | B06B 1/0611 604/22 |
| 6,533,750 B2 * | 3/2003 | Sutton | A61M 1/008 604/187 |
| 6,605,054 B2 | 8/2003 | Rockley | |
| 8,764,782 B2 * | 7/2014 | Akahoshi | A61F 9/00763 604/22 |
| 8,801,737 B2 * | 8/2014 | Akahoshi | A61F 9/00745 604/22 |
| 8,992,459 B2 * | 3/2015 | Nallakrishnan | 604/22 |
| 2002/0099325 A1 * | 7/2002 | Sutton | A61M 1/008 604/22 |
| 2003/0004455 A1 | 1/2003 | Kadziauskas | |
| 2004/0199192 A1 * | 10/2004 | Akahoshi | A61F 9/00745 606/169 |
| 2006/0052758 A1 * | 3/2006 | Dewey | A61F 9/00745 604/272 |
| 2006/0217672 A1 | 9/2006 | Chon | |
| 2007/0249942 A1 * | 10/2007 | Salehi | A61F 9/00745 600/471 |
| 2008/0058708 A1 * | 3/2008 | Akahoshi | A61F 9/00745 604/22 |
| 2008/0294087 A1 * | 11/2008 | Steen | A61F 9/00745 604/22 |
| 2009/0143795 A1 * | 6/2009 | Robertson | A61B 17/320092 606/169 |
| 2010/0010419 A1 * | 1/2010 | Akahoshi | A61F 9/00745 604/22 |
| 2011/0015561 A1 * | 1/2011 | Akahoshi | A61F 9/00745 604/22 |
| 2011/0112466 A1 * | 5/2011 | Dimalanta | A61F 9/00745 604/22 |
| 2011/0166502 A1 * | 7/2011 | Nallakrishnan | A61F 9/00745 604/22 |

OTHER PUBLICATIONS

Quality 101, Surface Analysis Beyond Roughness, Patrick Nugent published Apr. 25, 2008, pp. 1-7.

* cited by examiner

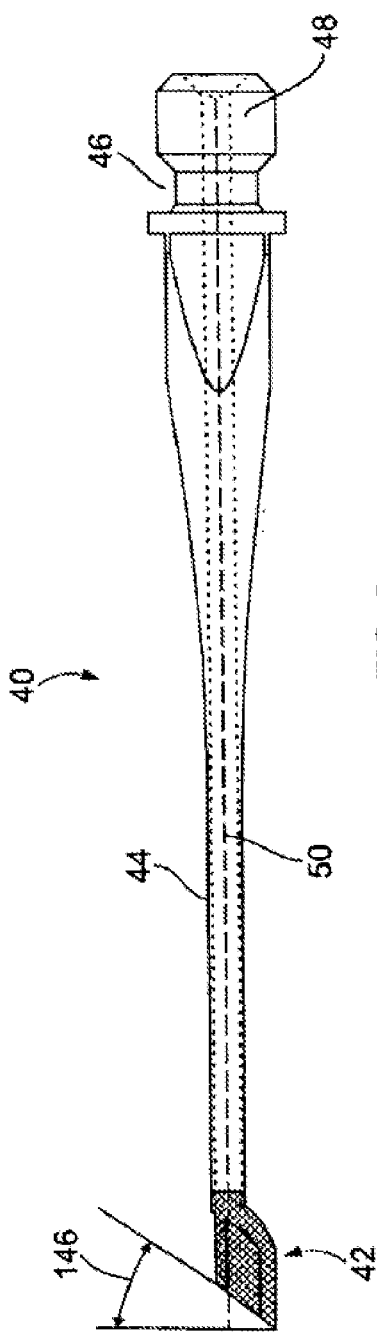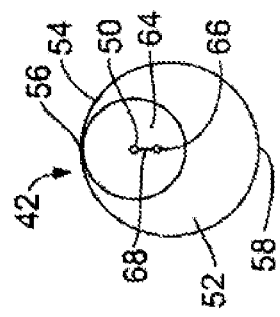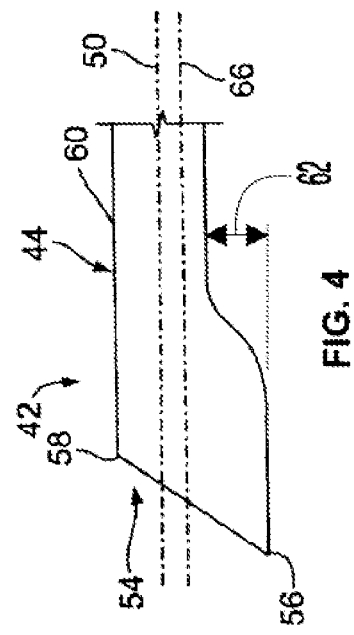

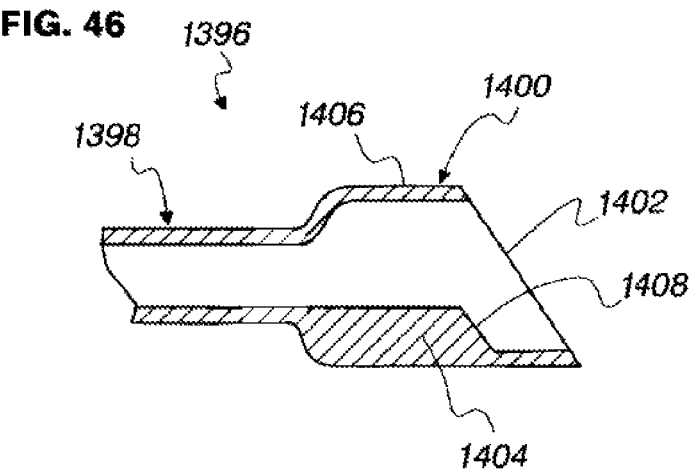
FIG. 46
FIG. 47
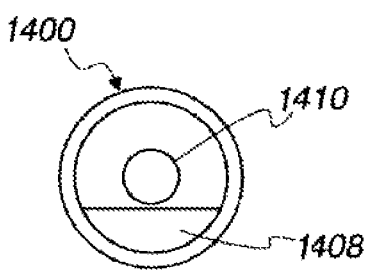
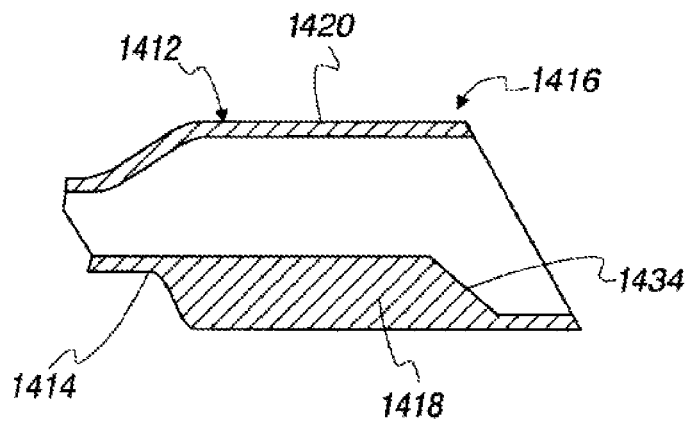
FIG. 48
FIG. 49
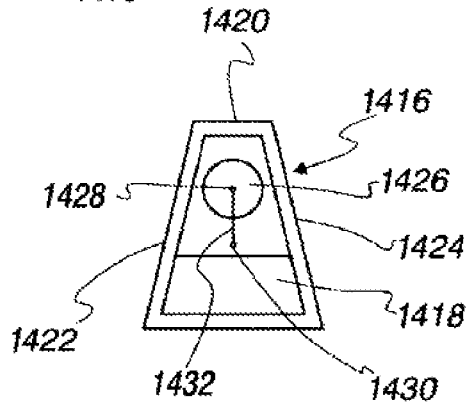

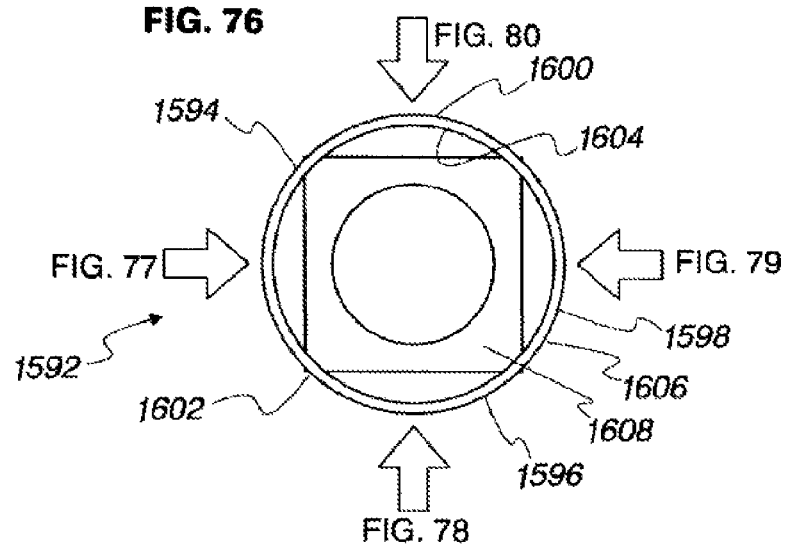
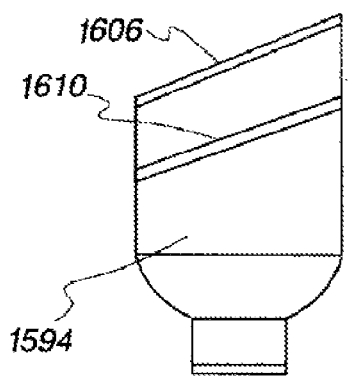
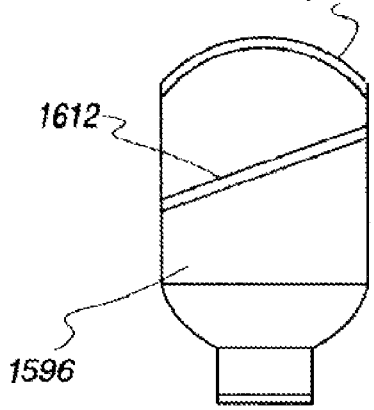
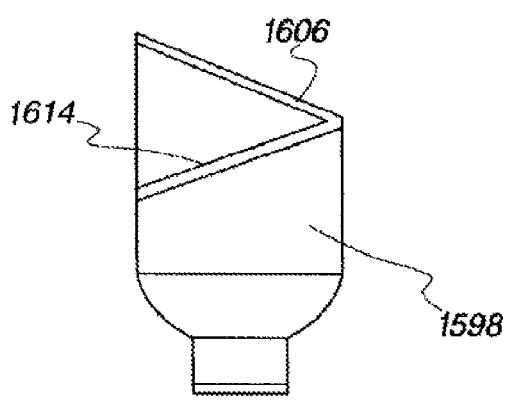
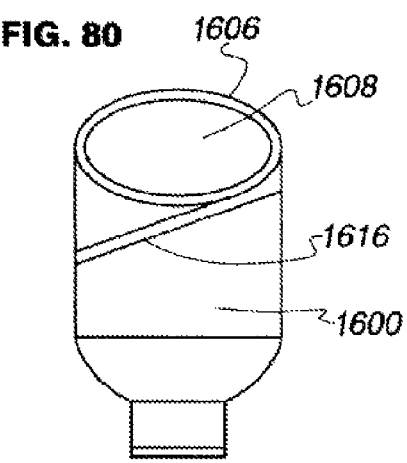

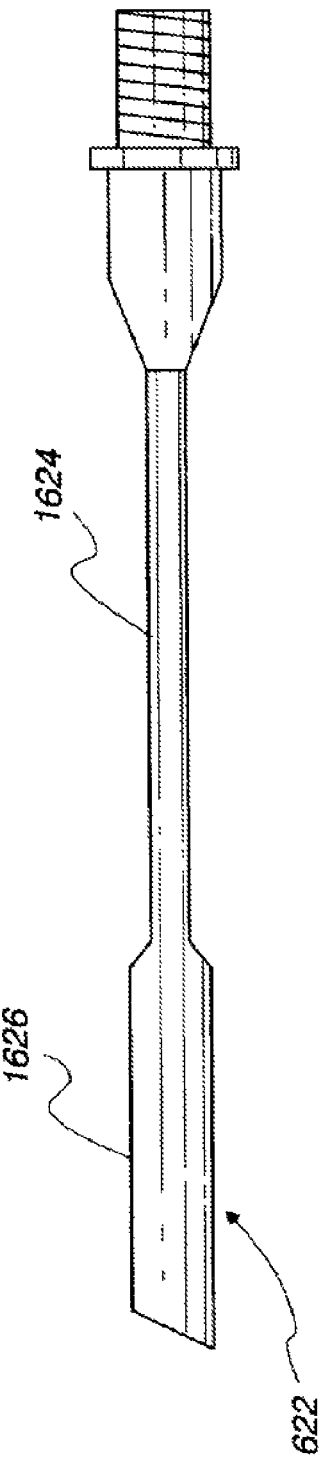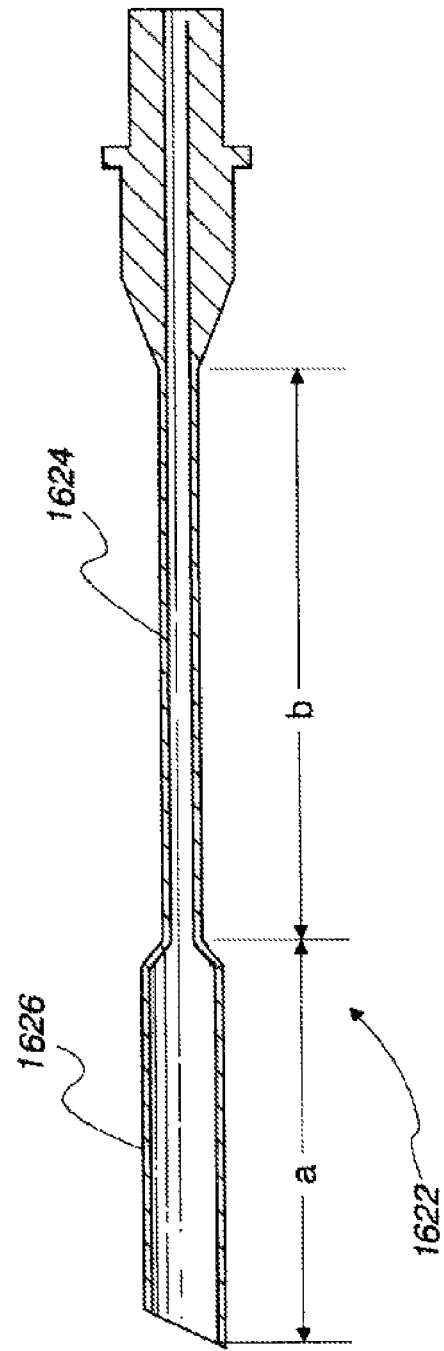
FIG. 83
FIG. 84

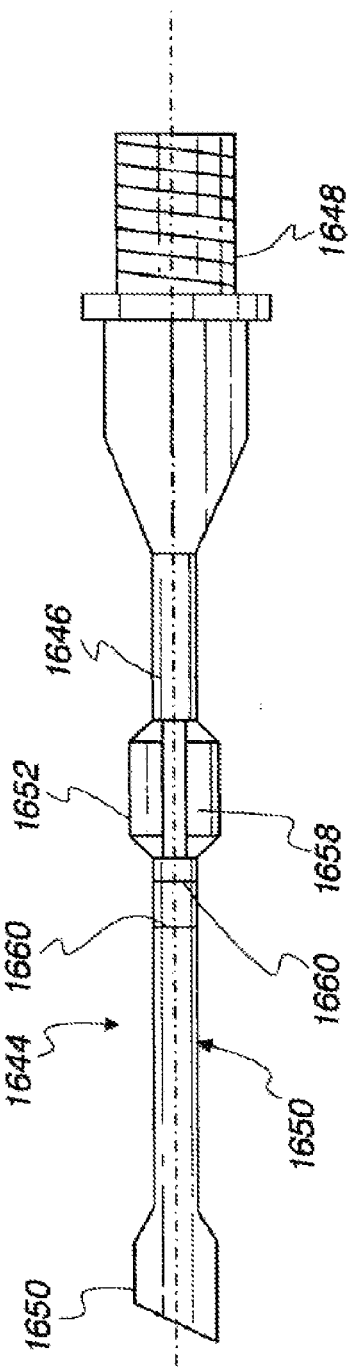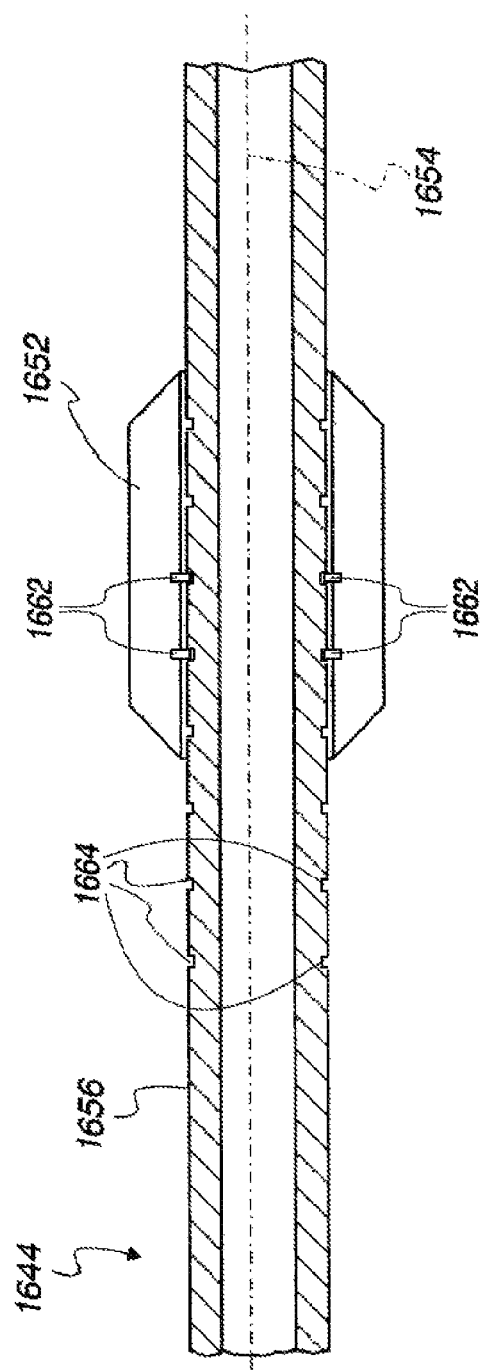
FIG. 87
FIG. 88

APPARATUS AND METHOD FOR PHACOEMULSIFICATION

This application claims priority from U.S. patent application Ser. No. 61/246,864 filed Sep. 29, 2009 and entitled "Apparatus and Method for Phacoemulsification", which is a continuation-in-part of application Ser. No. 12/263,315, filed 31 Oct. 2008, now U.S. Pat. No. 9,132,033 which is claims priority from application Ser. No. 60/984,375, filed 1 Nov. 2007, all of which are incorporated herein, by reference, in their entirety, for all purposes as is fully set forth herein.

FIELD OF THE INVENTION

This disclosure relates to surgical instruments and surgical techniques used in eye surgery and more particularly, to phacoemulsification apparatus and methods for their use.

BACKGROUND OF THE INVENTION

A common ophthalmological surgical technique is the removal of a diseased or injured lens from the eye. Earlier techniques used for the removal of the lens typically is required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such removal technique is known as phacoemulsification. A typical phacoemulsification tool includes a handpiece to which is attached a hollow needle. Electrical energy is applied to a piezoelectric crystal to vibrate the needle at ultrasonic frequencies in order to fragment the diseased lens into small enough particles to be aspirated from the eye through the hollow needle. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. Some benefits of using as small incision as possible during such surgery are the minimization of leakage of liquid during and after surgery to help prevent tissue collapse, faster healing time and decreased post-operative astigmatism.

Phacoemulsification needles and tips are well represented in the prior art. Needles and tips of varying configurations are well known. A particular shape for a tip or needle is often dictated by the type of handpiece with which the needle is to be used.

U.S. Pat. No. 5,725,495 (Strukel et al) teaches and describes a phacoemulsification handpiece, sleeve and tip illustrating a wide variety of tip configurations and needle cross-sectional configurations.

U.S. Pat. No. 6,007,555 (Devine) teaches and describes an ultrasonic needle for surgical emulsification. The needle and its tip are shown in both circular and oval configurations.

U.S. Pat. No. 6,605,054 (Rockley) teaches and describes a multiple bypass port phacoemulsification tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

U.S. Pat. No. 5,645,530 (Boukhny) teaches and describes a phacoemulsification sleeve, one variation of which has a bellows portion attached to a discharge port ring which directs an annular flow of liquid around the needle and into the eye. The use of the bellows is intended to, allow the sleeve to absorb spikes, in liquid pressure during the operation.

Published U.S. Patent Application No. 2003/0004455 (Kadziauskas) teaches and describes a bi-manual phacoemulsification needle using separate emulsification and aspiration needles inserted into the eye simultaneously during surgery.

Published U.S. Patent Application No. 2006/0217672 (Chon) teaches and describes a phacoemulsification tip that is swaged or crimped at its distal end. The tip is intended for use with a handpiece producing torsional motion and the crimping forms cutting edges at the distal end.

Many phacoemulsification needles and tips are designed for use with handpieces that vibrate the needle longitudinally at relatively low frequencies. In addition to, longitudinal vibration, certain handpieces sold by Alcon, Inc. of Ft, Worth, Tex. claim to impart a torsional motion to the needle at an oscillation vibration frequency of about 100 cycles/second. There are also handpieces that provide torsional oscillation of the phacoemulsification tip at frequencies of about 32,000 cycles/second.

Use of the torsional-type, handpiece has called for phacoemulsification needle tip designs differing from those used with the longitudinal-type handpiece. For example, needles having been designed with tips that are shaped, swaged, and angled to take advantage of the needle motion created by the handpiece.

Many surgeons favor phacoemulsification needles having the straight tip design commonly used with longitudinal hand pieces. The great majority of surgeons use longitudinal handpieces rather than torsional hand pieces, often because torsional phacoemulsification equipment is more expensive than longitudinal equipment, and thus find themselves unable to take advantage of the enhanced phacoemulsification results claimed in torsional phaco.

Forming a needle tip in an off-axis position relative to the axis of the aspiration passageway extending through the needle body causes eccentric, motion or "wobble" during torsional phacoemulsification and improves the efficiency of phacoemulsification while retaining the straight-tip configuration. Surprisingly, I have also found that forming the tip in such an off-axis position also increases the efficiency of phacoemulsification when using a longitudinal hand piece. Preliminary clinical examinations indicate that using an off-axis needle with a longitudinal hand piece may be more efficient than using the same needle with a torsional hand piece providing 100% torsional action, where efficiency is measured by the energy dissipated during phacoemulsification. When used herein, the term "dissipated energy" refers to the amount of energy, most commonly measured in joules, used by the hand piece during phacoemulsification. Lower dissipated energy readings mean that less heat is being produced during phacoemulsification which lowers the possibility of thermal damage to the delicate eye tissues.

There are known phacoemulsification apparatus, such as the Infiniti® Vision System manufactured by Alcon Laboratories of Ft. Worth, Tex. which allow the surgeon to choose between using torsional motion, longitudinal motion, or a blend thereof in a single hand piece. A common blended setting uses, torsional motion two-thirds of the time, and longitudinal motion one-third of the time. It is believed that the "blended" motion produces a more three-dimensional effect because of the back-and-forth motion imparted during longitudinal phacoemulsification and the eccentric motion produced at the tip during torsional phaco.

Use of an off-axis tip with a longitudinal hand piece appears to create a hybrid type of phacoemulsification motion without using the more complex and expensive torsional phacoemulsification apparatus. I have also determined that the eccentric or wobble type of motion can be imparted to a phacoemulsification needle with no flare at the tip by forming the central aspiration passageway within the needle body in an off-axis position. It is also expected that similar results will be obtained using a straight phacoemulsification needle having an aspiration passageway that is formed with a cross sectional configuration different than the cross-section configuration of the needle body itself, and that these results will be further amplified if the passageway is also placed off-axis.

While the following describes a preferred embodiment or embodiments of the present invention, it is to be understood that such description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

I have determined that an eccentric or "wobble" motion can be imparted to a phacoemulsification needle by constructed the needle to include anomalies in distribution of the needle's mass. In other words, the needle is manufactured in a manner in which the distribution of mass about the needle's major axis is not uniform.

In accordance with the preferred embodiment of the present invention, the needle itself is formed with the central aspiration passageway angles with respect to the central axis of the needle body.

In another embodiment the needle with an angled aspiration passageway is combined with a flared tip that is centered on the needle body.

In another embodiment, an off-axis aspiration passageway is combined with a needle tip wherein the tip itself is formed with non-uniform distribution of mass.

In yet another embodiment, the needle tip having a non-uniform distribution of mass is combined with a passageway that is coaxial with axis of the needle body.

In another embodiment a bump or selected number of bumps is formed on the external surface of the needle tip to create a non-uniform distribution of mass.

In yet another embodiment the portion of the needle is formed from a metal having a first density while the remaining portion is formed from a metal having a different density.

In yet another embodiment, the portion of the needle is drilled away and the resulting aperture is plugged with a metallic plug having a density different than that of the density of the main needle body.

In another embodiment, a series of needle tips having non-uniform skewed ridges on double beveled needle tips.

In another embodiment, a portion of the needle body is formed with a diameter larger than the remaining portion.

In another embodiment, the distal portion of the needle body is formed a larger diameter, a larger portion of which is offset.

BRIEF DESCRIPTION OF THE DRAWINGS

Further aspects of the present invention will be best understood by reference to the accompanying drawings in which like numbers are used to identify like parts, and which are presented to illustrate the aspects of the invention although not necessarily to actual scale, wherein:

FIG. 3 is a lateral schematic view of a phacoemulsification needle embodying the present invention;

FIG. 4 is a sectional view of the needle of FIG. 3;

FIG. 5 is an end view taken along 5-5 of FIG. 4;

FIG. 46 is a partial sectional view of another embodiment of an asymmetrical needle tip;

FIG. 47 is an end view of the tip of FIG. 46;

FIG. 48 is a partial sectional view of yet another embodiment of an asymmetric needle tip;

FIG. 49 is an end view of the tip of FIG. 48;

FIG. 76 is another embodiment of a tip having skewed and multiple bevels;

FIG. 77 is a view of a of FIG. 76;

FIG. 78 is a view at b of FIG. 76;

FIG. 79 is a view at c of FIG. 76;

FIG. 80 is a view at d of FIG. 76;

FIG. 83 is a lateral elevation of a phacoemulsification needle having an enlarged distal needle body portion;

FIG. 84 is a sectional view of the needle of FIG. 83;

FIG. 87 is a lateral elevation of a phacoemulsification needle having a symmetrical weight affixed to the needle body portion; and FIG. 88 is an enlarged partial sectional view of the needle of FIG. 87;

DETAILED DESCRIPTION OF THE INVENTION

Figure 1:
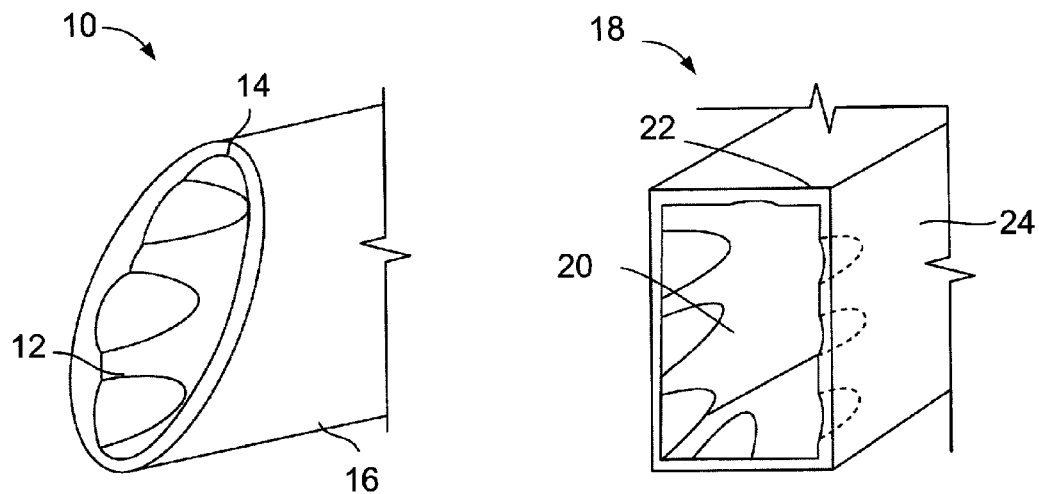
FIG. 1 is a drawing showing prior art straight oval- and square-shaped tips.

Referring now to FIG. 1, the numeral 10 indicates generally a prior art phacoemulsification needle tip as shown in U.S. Pat. No. 6,007,555 (Devine), entitled "Ultrasonic Needle for Surgical Emulsification", issued Dec. 28, 1999. Needle 10 is straight and terminates in an unflared mouth 12 defined by a lip 14 at the end of needle body 16, with lip 14 and needle body 16 formed as having an oval cross-section configuration.

Referring to FIG. 1, the numeral 18 indicates generally a prior art straight, unflared phacoemulsification needle tip from U.S. Pat. No. 6,007,555, having a mouth 20 defined by a lip 22 at the end of needle 24. The cross-sectional configuration of needle 18 and mouth 20 is a rectangle.

Figure 2:
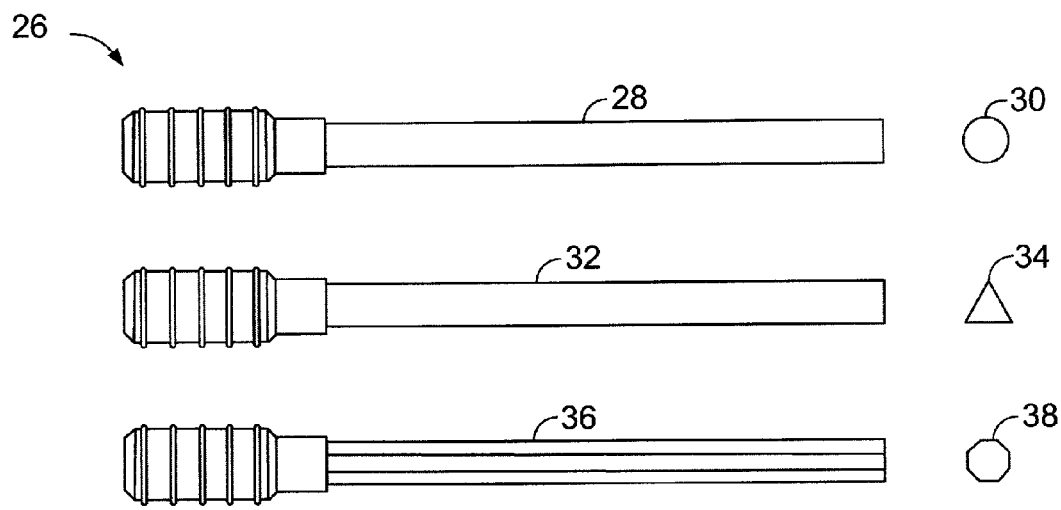
FIG. 2 is a drawing showing several prior art needle cross-sectional configurations.

Referring now to FIG. 2, the numeral 26 identifies several prior art straight phacoemulsification needles as described in U.S. Pat. No. 5,725,495, with needle 28 having a circular cross-section as shown at 30, needle 32 having a triangular cross-section as shown at 34 and needle 36 having an octagonal cross-section as shown at 38. As seen at 30, 34 and 38 of FIG. 2, needles 28, 32 and 36 have exterior shapes or cross-sections identical to the shape and cross-section of the aspiration passageways formed therethrough.

Both tips 10 and 18 in FIG. 1 exemplify one form of a "straight" needle tip, that is, a tip that is coaxial with or centered on the hollow aspiration passageway formed through the needle body and which have no flare or enlargement at the tip. Other straight tips are known which have needle tips that are flared, or larger in cross-sectional area than the needle's aspiration passageway yet which are centered on the passageway.

Phacoemulsification needles are sometimes referred to as "tips". Our use of the term "tip" throughout refers to that end of the needle intended to be inserted into the eye. The remaining portion of the phacoemulsification needle will generally be referred to as the needle body.

Referring now to FIG. 3, the numeral 40 indicates generally a phacoemulsification needle having a flared needle tip 42 larger in cross-section than and formed integrally with a distal end of a hollow needle body 44. At a proximal end thereof, needle body 44 has a needle end 46 which terminates in a mount 48 which allows needle 40 to be attached to a phacoemulsification handpiece. Commonly, mount 48 is threaded and screws onto a phacoemulsification handpiece. In the example shown, needle body 44 has a square cross-section with a longitudinally-extending central axis 50.

Referring now to FIG. 5, needle 40 is shown in lateral cross-section, illustrating the communication of aspiration passageway 64 with tip 42.

Referring now to FIG. 4, an enlarged detail of tip 42 is shown. As seen in both FIGS. 5 and 6, tip 42 has a mouth 52 defined by a lip 54 which, as shown in FIG. 3, is formed at an angle 146 to a plane that is normal to axis 50. The angle shown is one of choice: lip 54 can also be formed on the plane that is perpendicular to axis 50 or formed in any number of other configurations corresponding generally to the configurations of known straight tips presently used with longitudinally-vibrating hand pieces.

As viewed in FIG. 5, tip 42 has a lead portion 56 and a trailing portion 58, with lead portion 56 being that part of lip 54 that extends longitudinally forward past trailing portion 58, while trailing portion 58 is that part of lip 54 that extends the least distance forward. In the example shown in FIG. 5, trailing portion 58 is substantially co-linear with the outer surface 60 of needle body 44, while lead portion 56 is offset by a distance 62 from the outer surface 60 of needle body 44. The effect of forming lip 54 at the angle shown place lead portion 56 at the farthest point body axis 50.

Figure 6:
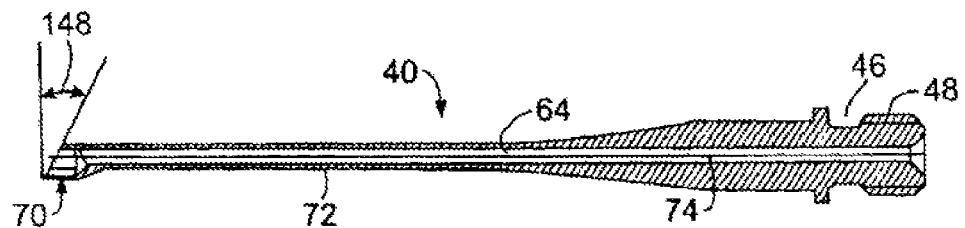
FIG. 6 is a partial lateral schematic view of the needle of FIG. 5.

Referring now to FIGS. 5 and 6, an aspiration passageway 64 of needle body 44 s shown centered on axis 50. Tip mouth 52 is shown defined by lip 54 with lead point 56 and training point 58. In the example shown, tip 42 has its own tip axis 66 extending therethrough. As seen in FIGS. 4 and 5, in this example, axes 50 and 66 do not coincide but are offset by a distance 68. As also seen in FIG. 6, the cross-sectional area of tip 42 is larger than the cross-sectional area of needle body 44 when viewed in a plane perpendicular to axis 50.

In a preferred example needle body 44 is 1.0 mm exterior diameter with a wall thickness of 0.10 mm, leaving an interior diameter of 0.80 mm. Tip 42 has an exterior diameter of 1.10 mm and a wall thickness of 0.10 mm. The lateral distance from the point at which tip 42 begins to enlarge outward from needle body 44 to lead point 56 is 1.80 mm, while offset distance 62 is 0.30 mm.

Figure 7:
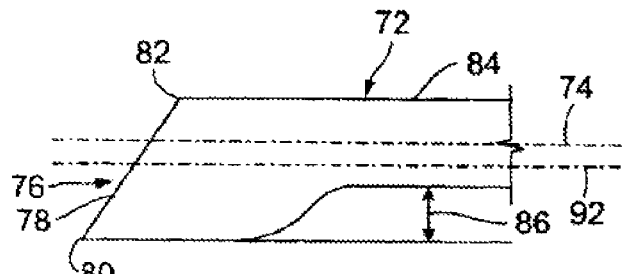
FIG. 7 is a lateral view of a needle tip having a circular cross-section.
Figure 8:
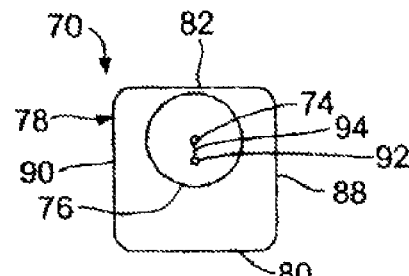
FIG. 8 is a partial lateral schematic view of the needle tip of FIG. 7.

Referring now to FIGS. 7 and 8, a second example of a needle tip formed on needle 40 is shown. Needle tip 70 is square in cross-sectional shape and is formed integrally with a hollow needle body 72. In this example shown, needle body 72 has a circular cross-section with a longitudinally-extending central axis 74.

Referring to FIG. 7, an enlarged detail of tip 70 is shown. As seen in both FIGS. 7 and 8, tip 70 has a mouth defined by a lip 78 which, in the example shown in FIG. 7, is formed at an angle 148 to axis 74. The angle shown is one of choice: lip 78 can also be formed perpendicular to axis 74 or any number of other configurations corresponding generally to the configurations of known straight tips presently used with longitudinally-vibrating hand pieces.

As viewed in FIG. 7, tip 70 has a lead lip portion 80 and a trailing lip portion 82, with lead portion 80 being that part of lip 78 that extends longitudinally past trailing portion 82, while trailing portion 82 is that part of lip 78 that extends the least distance longitudinally forward. In the example shown in FIG. 7, trailing lip portion 82 is substantially co-linear with the outer surface 84 of needle body 72. The effect of forming lip 78 at angle 148 is to place lead lip portion 80 farthest from needle body axis 74.

Referring now to FIG. 8, the interior of needle body 72 is shown. Needle body 72 has a central aspiration passageway 76 extending therethrough, centered on axis 74. In the example shown, tip 70 has its own central axis 92, which, as seen in FIGS. 7 and 8 is offset from needle body axis 74 by a distance 94. As also seen in FIG. 8, the cross-sectional area of tip 70 is greater than the cross-sectional area of needle body 72 when viewed in a plane perpendicular to axis 74.

Figure 9:
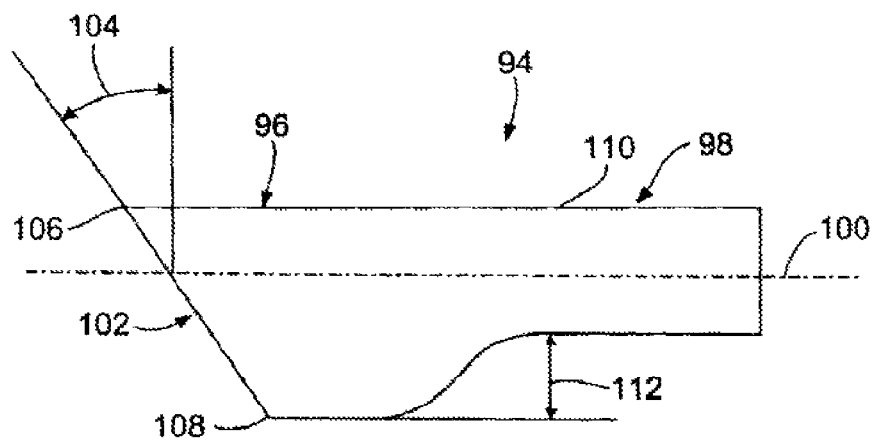
FIG. 9 is a partial lateral view of a variation of the tip shown in FIG. 6.

Referring now to FIG. 9 the numeral 94 identifies a phacoemulsification needle constructed substantially as described with respect to FIGS. 3, 4, 5, and 6. Needle 94 has a tip 96 formed with a circular cross-section and integral with needle body 98. Needle body 98 has a central axis 100.

Tip 96 has a square mouth 102 which, in this example, is formed at an angle 104 to axis 100. In this example, angle 104 is measured 30° in a direction opposite to that of angle 146 of mouth 52 as shown in FIG. 3. This angle is a matter of choice and other angles can be used as well. In this configuration, tip 96 has a lead point 106 and a trailing point 108, corresponding in description to points 56, 58 described above. In this example, lead point 106 is collinear with outer surface 110 of needle body 98 while trailing point 108 is offset from outer surface 110 by a distance 112.

Figure 10:
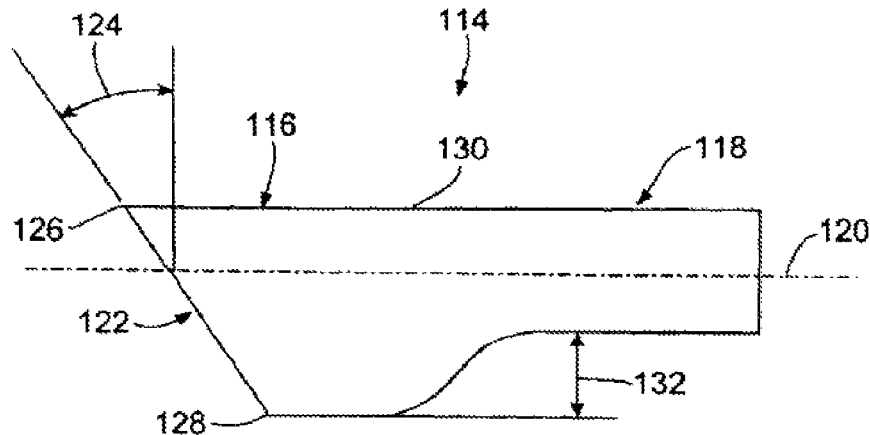
FIG. 10 is a partial lateral view of a variation of the tip shown in FIG. 8.

Referring now to FIG. 10 the numeral 114 identifies a phacoemulsification needle constructed substantially as described with respect to FIGS. 7 and 8. Needle 114 has a tip 116 formed with a circular cross-section and integral with needle body 118. Needle body 118 has a central axis 120.

Tip 116 has a circular mouth 122 which, in this example, is formed at an angle 124 to a plane normal to axis 120. In this example, angle 124 is measured 30° in a direction opposite to that of angle 148 of mouth 74 as shown in FIG. 6. In this configuration, tip 116 has a lead lip portion 126 and a trailing lip portion 128, corresponding in description to lip portions 80, 82 described above. In this example, lead lip portion 126 includes a portion of outer surface 130 of needle body 118 while trailing lip portion 128 is offset from outer surface 130 by a distance 132.

Figure 11:
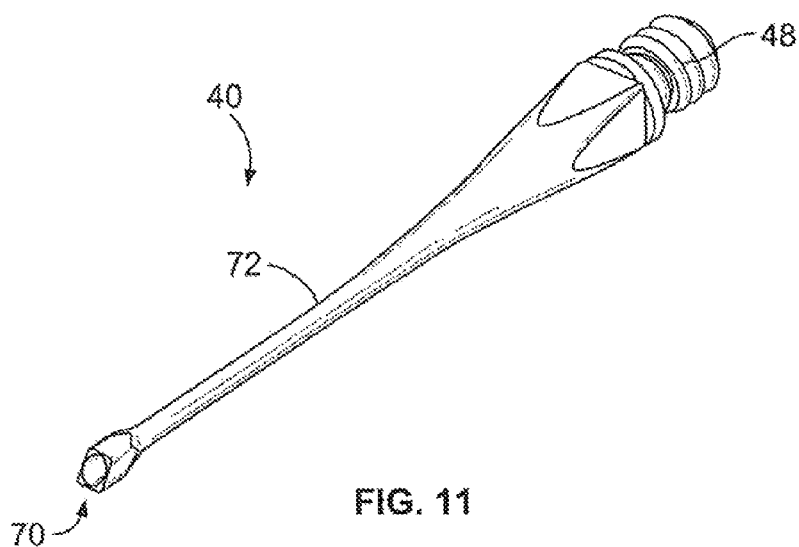
FIG. 11 is a perspective view of the needle of FIG. 3.
Figure 12:
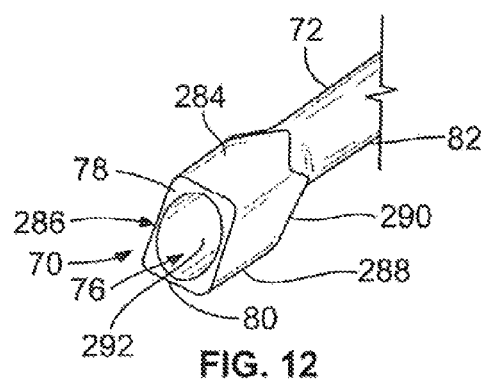
FIG. 12 is an enlarged view of the tip of FIG. 11.
Figure 13:
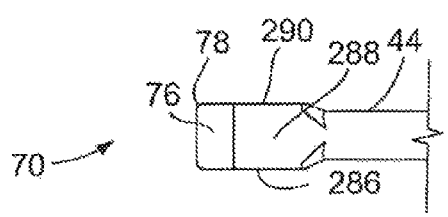
FIG. 13 is a bottom view of FIG. 12.

Referring now to FIG. 11, a perspective view of needle 40 is shown with needle body 72 terminating at one end of tip 70 and at the other end at threaded mount 48. FIG. 12 is an enlarged perspective view of tip 70 showing the square configuration of, leading and trailing portions 78, 80. FIG. 13 is a bottom view of tip 70.

Figure 14:
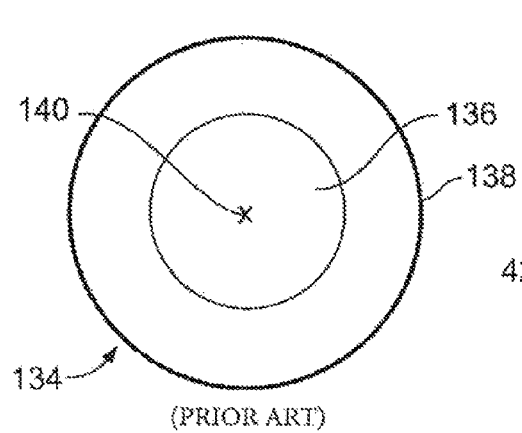
FIG. 14 is an illustration of the end of a prior art straight needle tip during torsional motion.
Figure 15:
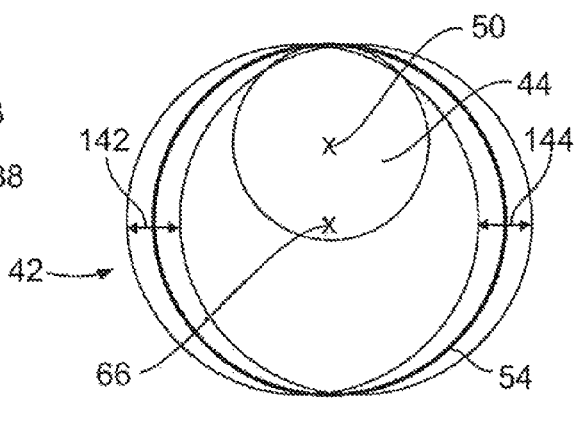
FIG. 15 is an illustration of the and of a needle tip constructed in accordance with the present invention and used with torsional motion.

The efficacy of having the tip axes in each of the foregoing examples be non-coincident with, or offset from, the needle body axes is demonstrated in FIGS. 14 and 15. Using a circular tip as an example, the numeral 134 in FIG. 14 identifies a prior art straight phacoemulsification tip having a circular cross-section defined by mouth 136 integral with and extending from needle body 138. Hollow needle body 138 has a central, longitudinally-extending axis 140. The geometry of tip 134 is such that axis 140 is also a central, longitudinally-extending axis for tip 134. When needle body 138 with tip 134 is attached to a phacoemulsification handpiece that produces torsional motion about axis 140 the pattern of vibration is generally as shown in FIG. 14, with tip 134 exhibiting little side-to-side or eccentric motion. In other words, lip 36 tends to move in a generally uniform motion about axis 140.

Referring now to FIG. 15, tip 42 of FIG. 4 is shown, with circular lip 54 and a needle body axis 50 and tip axis 66. When tip 42 is subjected to torsional or longitudinal motion, lip 54 moves eccentrically, or "wobbles", in part because tip 42 has a rotation that is not centered on tip axis 66. This produces movement of lip 54 shown by paths 142 and 144, creating an enhanced cutting or emulsifying effect on the tissue contacted by tip 42. Thus, a straight phacoemulsification needle with a flared tip can be used with torsional or longitudinal motion.

The "wobble" effect can be altered by changing the offset distance between the tip axis and the needle body axis, and by changing the geometry of the tip, by using different cross-sectional shapes such as triangular or polygonal.

Figure 16:
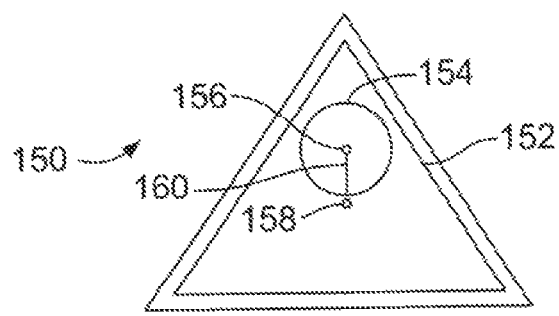
FIG. 16 is an end view showing a needle having a triangular offset tip.

Referring now to FIG. 16, the numeral 150 identifies a phacoemulsification tip having a triangular cross-sectional configuration terminating at a lip 152 and communicating with a needle aspiration passageway 154 having an axis 156. Tip 150 has a central tip axis 158 offset from axis 156 by an offset distance 160.

Figure 17:
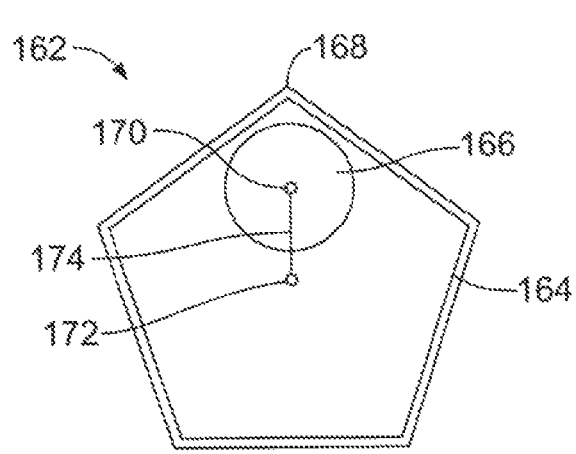
FIG. 17 is an end view of a needle having a pentagonal offset tip with the aspiration passageway formed at an apex to adjacent sides of the pentagon.

Referring now to FIG. 17, the numeral 162 identifies a phacoemulsification tip having a pentagonal cross-section terminating at a lip 164. Tip 162 communicates with a needle aspiration passageway 166 proximate apex 168. Passageway 166 has a central axis 170 and a tip 162 has a central axis 172 offset from axis 170 by an offset distance 174.

Figure 18:
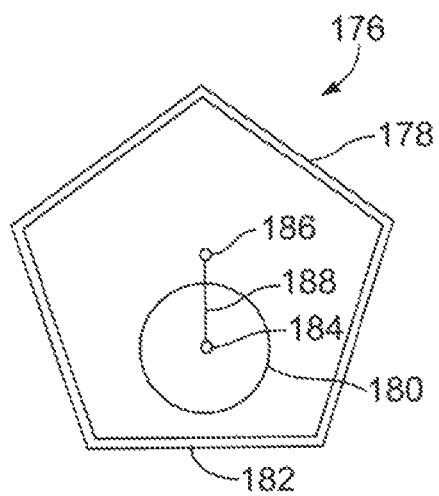
FIG. 18 is a view of FIG. 17 showing the aspiration passageway positioned along one side of the pentagonal tip.

Referring now to FIG. 18, the numeral 176 identifies a phacoemulsification tip having a pentagonal cross-sectional shape terminating in a lip 178. A needle aspiration passageway 180 extends to tip 176 proximate tip wall 182. Passageway 180 has a central axis 184 while tip 176 has a central axis 186 offset form axis 184 by offset distance 188.

Figure 19:
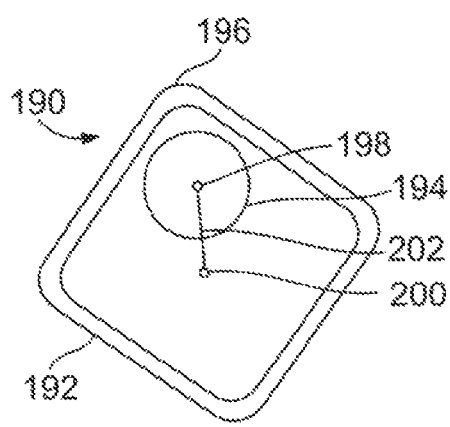
FIG. 19 is an end view of a square tip showing the aspiration passageway positioned at an apex of two adjacent sides of the square.

Referring now to FIG. 19, the numeral 190 identifies a phacoemulsification tip having a square cross-sectional shape terminating in a lip 192. A needle aspiration passageway 194 is formed proximate apex 198 of tip 192. Passageway 194 has a central axis 198 while tip 190 has a central axis 200 offset form axis 198 by an offset distance 202.

Phacoemulsification tips may also be formed on needle bodies that are non-circular in cross-section.

Figure 20:
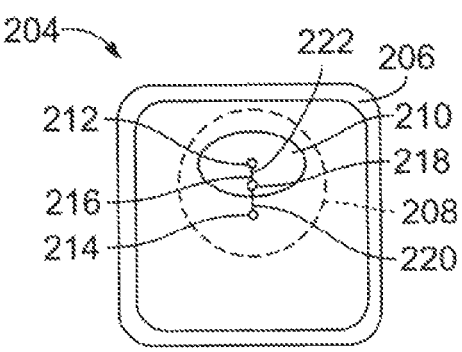
FIG. 20 is an end view of a square tip extending from a needle body having a circular outer cross-section and an aspiration passageway with an oval cross-section.

Referring now to FIG. 20, the numeral 204 identifies a phacoemulsification tip having a square cross-sectional shape terminating in a lip 206. Tip 204 extends from a needle body 208 having a circular cross-sectional shape. Needle body 208 has an oval-shaped needle aspiration passage 210 having a central axis 212 while tip 204 has a central axis 214 offset from axis 212 by an offset distance 216.

The forgoing examples have shown tips with flared shapes, that is, tips with cross-sectional shapes that are larger in size than the cross sectional shape of the needle body. Similar results are predicted for certain phacoemulsification needles with no flared tip that is the terminus of the needle is the same cross-sectional shape as the needle body.

Figure 21:
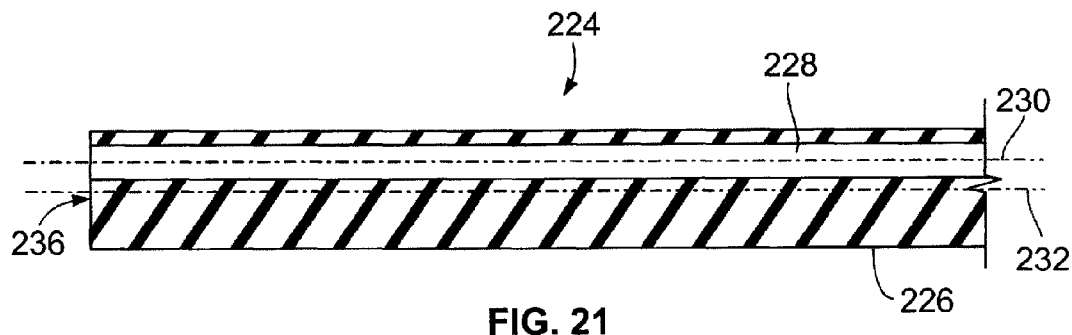
FIG. 21 is a lateral sectional view of a portion of a straight, unflared phacoemulsification needle having a circular exterior cross-section shape and an internal aspiration passageway having an oval cross-sectional shape.
Figure 22:
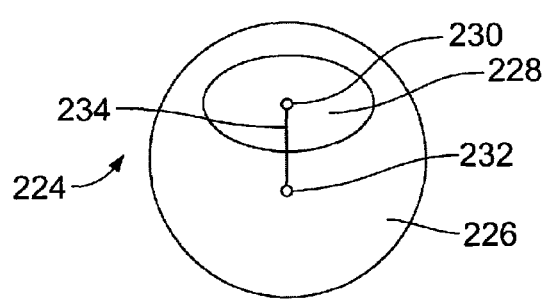
FIG. 22 is an end view of the needle of FIG. 21.

Referring now to FIG. 21, the numeral 224 identifies a straight phacoemulsification needle having a needle body 226 through which an aspiration passageway 228 is formed. As shown in FIG. 22, passageway 228 has an oval cross-sectional shape and has a central axis 230. Needle body 226 has a central axis 232 offset from passageway axis 230 by an offset distance 234.

Figure 23:
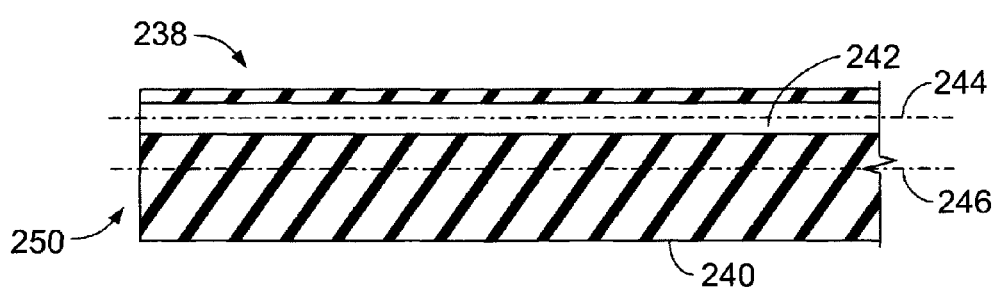
FIG. 23 is a lateral sectional view of a portion of a straight, unflared phacoemulsification needle having an oval cross-sectional shape with an aspiration passageway having a circular cross-sectional shape and offset toward one end of the needle body.
Figure 24:
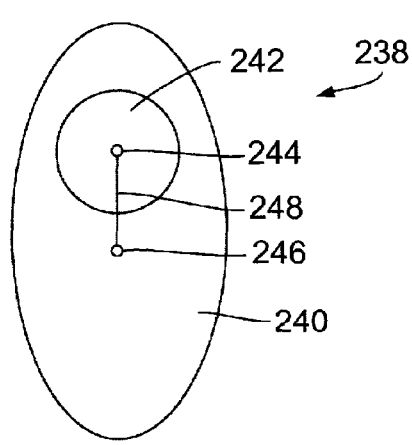
FIG. 24 is an end view of the needle of FIG. 23.

Referring now to FIG. 23, a straight phacoemulsification needle 238 has a needle body 240 formed with an oval cross-section. Passageway 242 has a central axis 244 and needle body 240 has a central axis 246 offset from axis 244 by an onset distance 248.

While the needle bodies referred to in the foregoing examples have been referred to as circular in cross-section it should be understood that different cross-sectional shapes can also be used.

The foregoing examples have demonstrated round and square eccentric tips. Other tip cross-sectional shapes can also be used and the tips can be made with various orientations. For example, tip 70 can be rotated around tip axis 92 to create a different orientation. It is expected that the wobble effect will be manifested when the axis of the tip is offset from the axis of the needle body no matter what configuration is used.

Lips such as those shown at 50 and at 78 may also be polished to a smooth finish to add a protective feature. Phacoemulsification efficacy may also be enhanced by roughening a portion of the outer surface of the tips herein detailed.

Offsetting the tip of an angled phacoemulsification needle tip increases efficiency as compared to a symmetrically fashioned tip. Phacoemulsification needles having flared tips that are angled with respect to the needle body are known in the art. Heretofore, such tips have been formed such that the bent portion of the needle body met the flared tip such that the tip was symmetrical about the needle body.

Figure 25:
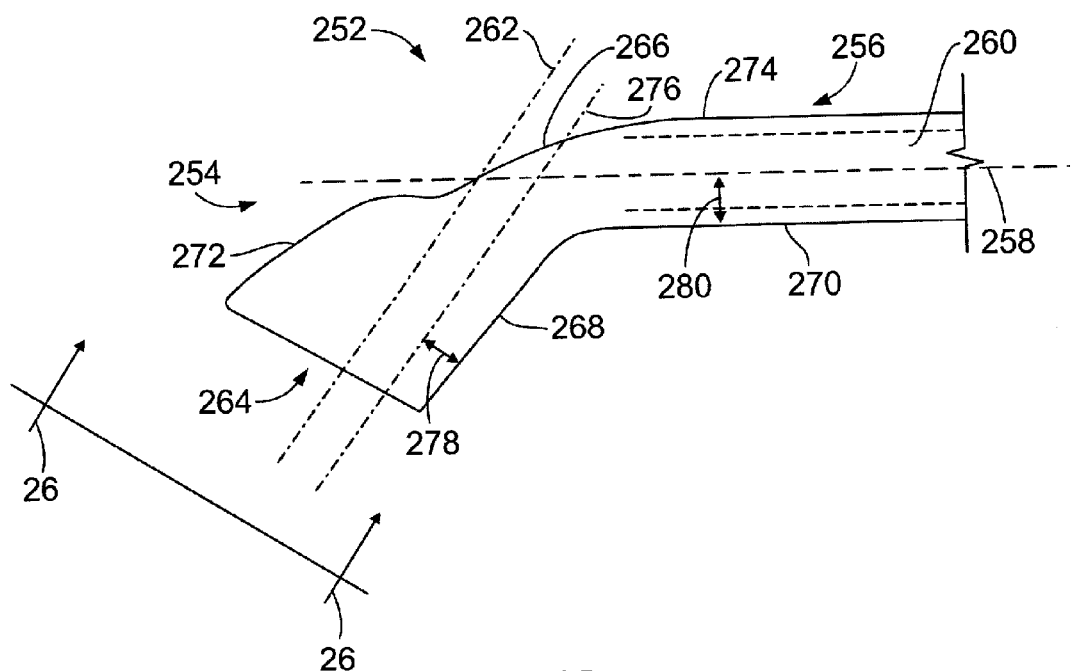
FIG. 25 is a lateral view of a phacoemulsification needle with an angled tip formed off-axis to the needle body.

Referring now to FIG. 25 the numeral 252 identifies a portion of a phacoemulsification needle which includes a tip 254 and a needle body 256. Needle body 256 has a longitudinal axis 258 and an aspiration passageway 260 extending along its length. Tip 254 has an axis 262 that is centered on the tip opening 264. In this example, the tip has a square cross-section.

A bend 266 is formed on needle body 256 and, as shown in FIG. 25, tip 254 is formed with a first wall portion 268 that is coextensive with bend 266 and first needle body portion 270. Tip 254 has a second wall portion 272 that is offset from bend 266 and needle bodyportion 274. Secondary needle body axis 276 is shown as positioned the same distance 278 from first wall portion 268 as the distance 280 that axis 258 is positioned from first needle body portion 270.

Figure 26:
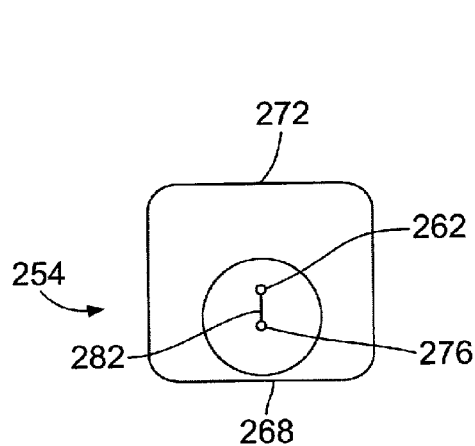
FIG. 26 is a view along 26-26 of FIG. 25.

Referring now to FIG. 26, an end view of tip 254 is shown takes as a view perpendicular to line 26-26 of FIG. 25. Axes 276 and 262 are shown to offset one from the other by a distance 282. This offset increases the eccentric motion exhibited by tip 254 and makes phacoemulsification more efficient.

The safety and efficiency of phacoemulsification tips embodying the foregoing aspects of the present invention are enhanced when the inner and outer surfaces of the phacoemulsification tip is roughened, as by sandblasting, and where the lip of the tip mouth is polished to round the lip and remove burrs which can damage delicate tissue in the eye, such as the posterior capsule, which may be contacted by the needle tip during phaco.

The square tip 70 shown in FIGS. 11, 12, and 13 is exemplary of the type of surfaces to which the roughening process is applied.

As seen in FIG. 12, tip 70 has an upper face 284, a left lateral face 286, a lower face 288 and a right lateral face 290. The identifiers "left" and "right" are used here to designate those faces as seen by one viewing FIG. 12. As can be appreciated, tip 70 has four external faces, all of which are roughened, beginning at and extending away from lip 78.

As further seen in FIG. 12, tip 70 has an inner tip surface 292 extending rearward toward needle body 72 and aspiration passageway 64. It is a feature of the present invention that the inner tip surface 292 is also roughened, as by sandblasting. The inner and outer surfaces of tip 70 are modified by roughening to create an uneven geometry providing numerous projections which are engaged by the tissue being emulsified as tip 70 is driven in its eccentric, or "wobble" motion.

Figure 27:
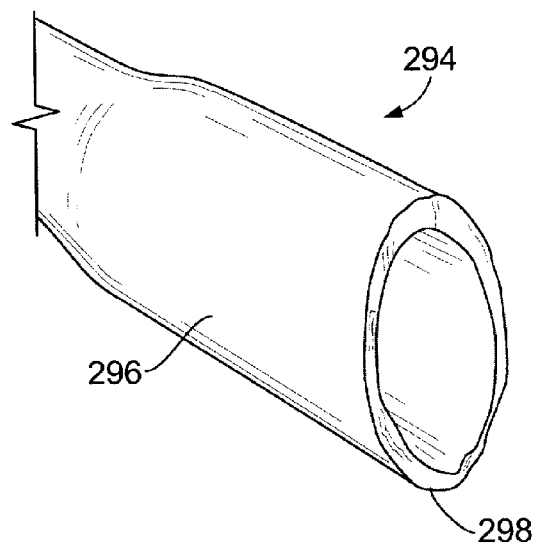
FIG. 27 is an enlarged view of a flared phacoemulsification needle tip.

It is another feature of the present invention to enhance the safety of the tips described herein by highly polishing the lip of each. Referring to FIG. 27 the numeral 294 identifies a phacoemulsification needle having a flared tip 296 terminating at a lip 298. In the example shown, tip 296 has a circular cross-section but the following description applies to the various tips of varying geometry described herein. Tip 296 is intended to be representative of phacoemulsification tips as customarily manufactured. Tip 296 is shown in a magnified view.

Figure 28:
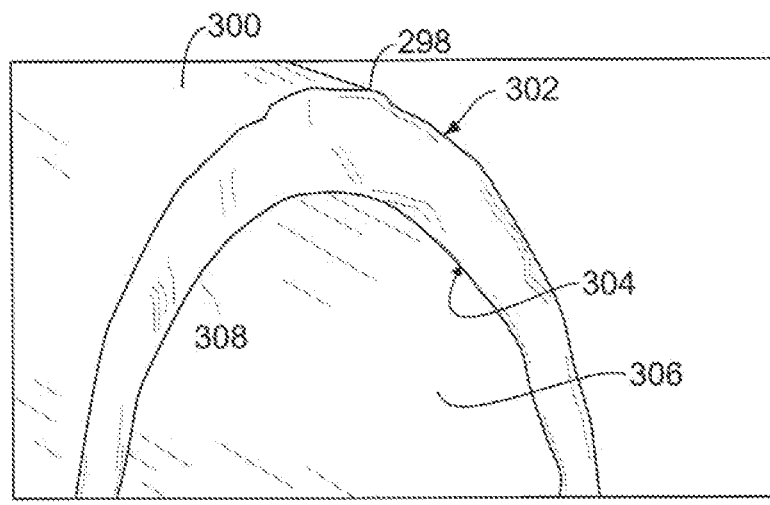
FIG. 28 is an enlarged view of FIG. 27.

A portion of lip 298 is seen in FIG. 28 in a more highly magnified view. The surface 300 of lip 298 is seen to meet tip 296 at substantially a right angle, forming a roughened edge 302. The same configuration creates a roughened edge 304, formed where lip surface 300 and tip inner surface 306 meet. Tip surface 300 is also characterized by upstanding ridges such as those identified by the numeral 308.

Edges 302 and 304, and ridges 308 are somewhat analogous to the "flashing" or "burrs" created when metallic workpieces are cut or severed. Because of the relatively thin metallic material from which phacoemulsification needles are formed, such edges and ridges are themselves thin and sharp, certainly sharp enough to snag corneal tissue when a phacoemulsification needle is inserted through a corneal incision. They are also sharp enough to damage delicate eye tissue, such as the posterior capsule, if the needle tip is brought into contact with the capsule during surgery.

I have determined that a process of rounding and highly polishing and smoothing the lips of phacoemulsification needle tips of the type described herein reduces the likelihood that delicate eye tissue will be damaged during phaco, particularly if the needle is being sued with a handpiece that produces torsional or elliptical motion.

Figure 29:
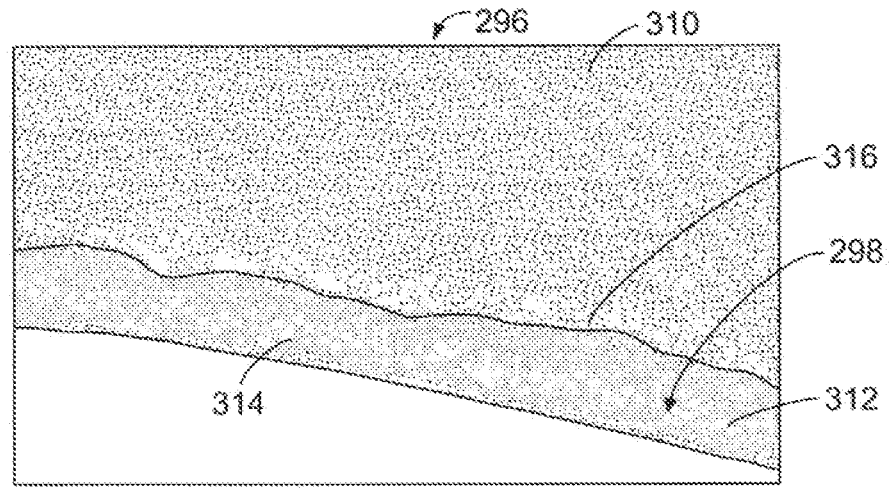
FIG. 29 is a microscopic view of a portion of the outer surface of the tip of FIGS. 27 and 28 after roughening and polishing.

Referring now to FIG. 29 the numeral 310 identifies the outer surface of tip 296 after a roughening procedure has been performed. As can be seen, surface 310 is "pitted" to create a much larger surface area for contact with tissue to be phacoemulsified.

FIG. 29 also shows a portion 312 of lip 298 after polishing. Lip surface 314 now meets outer surface 310 at a rounded edge 316, much smoother and snag-free than the roughened edge 302 shown in FIG. 28.

Figure 30:
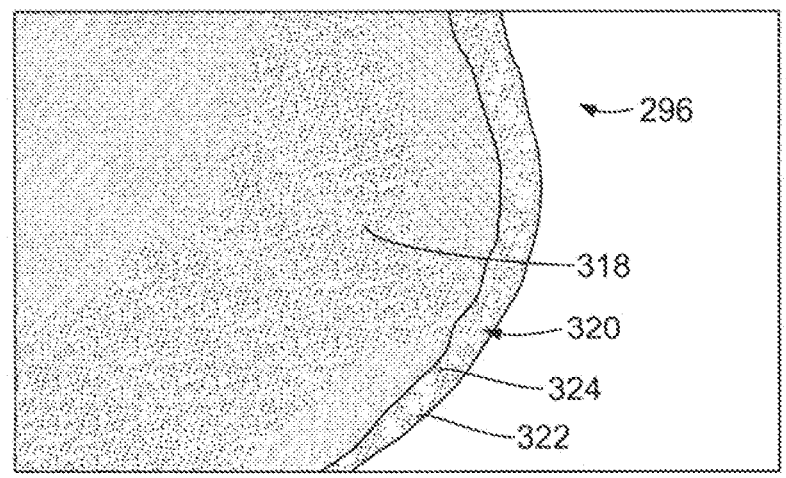
FIG. 30 is a microscopic view of a portion of the inner surface of the tip of FIGS. 27 and 28 after roughening and polishing.

In like fashion, a portion of inner surface 318 of tip 296 is shown after a roughening procedure has been performed. FIG. 30 also shows a portion 320 of lip 298 after polishing. Lip surface 322 now meets inner surface 318 at a rounded edge 324, such smoother and snag free than the roughened edge 304 shown in FIG. 28.

The elements of surface finish are described by Quality Magazine as form, waviness and roughness. These elements, as they are present in the surface finish on the lips of the needles described herein, are rounded and smoothed to a degree sufficient to avoid the snagging of the tip on tissue in the eye, particularly the tissue through which the corneal incision is made and the tissue forming the capsular bag.

While the roughening procedure has been preferably described as sandblasting, other types of operations to create a controlledly roughened surface may also be used. In like fashion, other forms of polishing or smoothing devices and procedures can also be used to satisfactorily prepare the lip of each such phacoemulsification needle tip.

Figure 31:
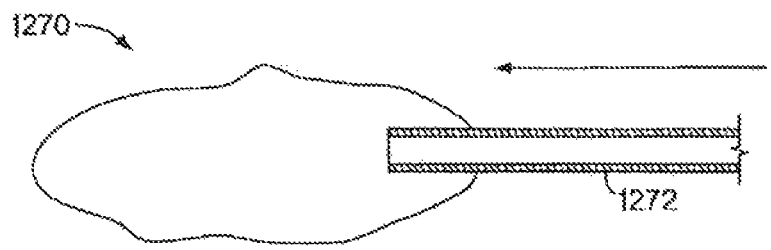
FIG. 31 is a partial lateral view of a prior art phacoemulsification needle in contact with a nucleus.
Figure 32:
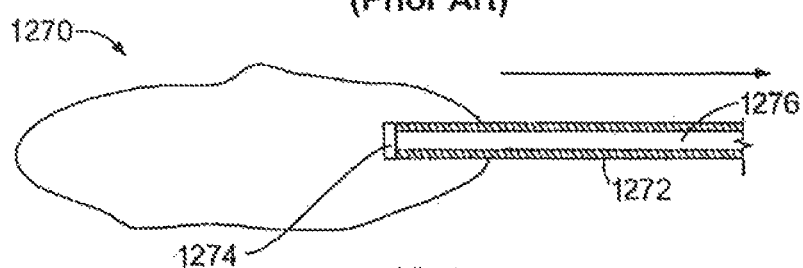
FIG. 32 is another partial lateral view of the prior art phacoemulsification needle shown in FIG. 31.

Referring now to FIGS. 31 and 32, the numeral 1270 identifies generally a lens nucleus undergoing phacoemulsification using a conventional phacoemulsification handpiece imparting only longitudinal motion to straight phacoemulsification needle 1272. As described previously, in longitudinal phacoemulsification a needle 1272 is alternately moved in forward and reverse directions at high speed. Phacoemulsification is more efficient when needle 1272 is in contact with nucleus 1270, particularly with traditional longitudinal phaco, because, as seen in FIG. 31, the cutting of nucleus 1270 occurs when needle 1272 moves forward to contact nucleus 1270. When the needle is drawn in the reverse direction it tends to lose contact with nucleus 1270, creating a gap 1274.

The procedure has several readily noticeable consequences. The forward motion and subsequent contact of needle 1272 with nucleus 1270 can repulse nucleus 1270 and also the fragments into which nucleus 1270 is cut, making more difficult and time-consuming the collection of the fragments through aspiration passageway 1276.

During phaco, viscoelastic support gel is injected into the lens capsule and the anterior and posterior chambers of the eye. One example of such a gel is Staarvisc© II, manufactured by Staar Surgical Company of Monrovia, Calif. Presence of a gel in the lens capsule helps support and protect the thin walls of the capsule. Using gel, in the posterior chamber helps protect the delicate endothelial cells which, if damaged, do not regenerate. During surgery, movement of the gel is readily noticeable when needles such as needle 1272 are vibrating. In particular, it can be seen that the gel present in the posterior chamber of the eye is moved or agitated even though needle 1272 is within the lens capsule.

As a general rule, the longer a phacoemulsification procedure lasts the more energy is expended and the more heat is produced by the ultrasound energy imparted to the needle. More efficient phacoemulsification is accomplished when the lens is fragmented more quickly, the fragmented lens particles are aspirated more quickly and cleanly and less heat is produced. As previously described, one measure of efficiency is the total dissipated energy: less energy is used if the procedure is shorter and one of the ways the procedure can be shortened is to make aspiration more effective. Another measure of efficiency is to observe such occurrences as the uninterrupted aspiration of particles and the "quietness" of the operating environment, meaning the relative lack of turbulence observed in the supporting gel, both in the lens capsule and the posterior chamber. This lack of turbulence can be quite important when, for example, a surgeon is required to use a less than optimal support material, one that may be more susceptible to breakdown during high speed vibration. One such substance is methyl cellulose which is not as viscous or cohesive as a gel such as Staarvisc© II.

Preliminary clinical observations have confirmed that the use of an off-axis phacoemulsification needle with a handpiece producing longitudinal motion results in significantly more efficient phaco. Operation times have been shorter, dissipated energy levels have been lower and the operating environment has been observed to be quieter, with much less agitation of the supporting gel and much less repulsion of the fragmented lens particles. This has resulted in markedly "clear" phacoemulsification results, meaning that the capsule is clearer of unaspirated particles and the supporting gel has provided better protection to the capsule and the endothelial cells.

An ultrasonic handpiece providing longitudinal and torsional motion to a phacoemulsification needle is described in United States Patent Publication 2006/0036180 (Boukhny, et al.), entitled "Ultrasonic Handpiece". As the application states, the two modes cannot be activated simultaneously: the handpiece is switchable between the torsional and longitudinal modes. A computer-controlled console allows the surgeon to select alternating time periods for torsional and longitudinal motion, resulting in an effective "blended" motion. The characteristic of such a blended motion are altered when the time periods are altered. For example, a different cutting action and cutting characteristics will result when torsional motion comprises 50 per cent of the operating time than when it comprises 75 per cent.

A phacoemulsification control system described in United States Patent Publication 2008/0294087 (Steen, et al.), assigned to Advanced Medical Optics, Inc. of Santa Ana, Calif. describes a system that imparts a longitudinal motion and lateral motion to the needle by forming the needle with an asymmetric needle mount. Such an arrangement is believed to exhibit certain characteristics of traditional longitudinal phaco, such as the tendency for the needle to lose frontal contact with the nucleus when the needle is moved away from the nucleus, the repulsion of nuclear particles and the tendency to transmit energy to agitate the viscoelastic gel inserted into the eye.

Combining an off-axis tip with a handpiece utilizing longitudinal motion appears to create a hybrid type of tip activity that exhibits some of the characteristics of this blended motion yet exhibits marked improvements in efficiency over systems which utilize modifications to longitudinal handpieces to achieve blended motion.

A phacoemulsification needle having an off-axis construction is mounted to a phacoemulsification handpiece capable of producing longitudinal motion. The geometry of the needle can include needle bodies with centered or off-axis aspiration passageways, needle bodies with centered or off-axis aspiration passageways having different cross-sectional shapes than the needle bodies, with such needles having straight or angled needle tips formed off-axis to the needle body aspiration passageway, with such tips being flared or unflared.

Figure 33:
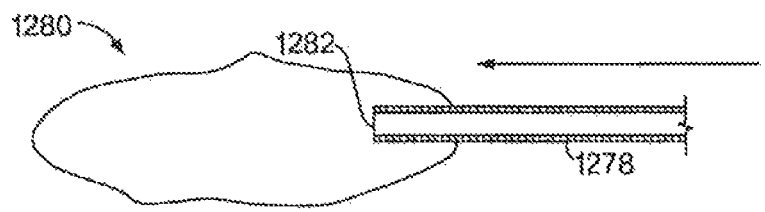
FIG. 33 is a partial lateral view of a phacoemulsification needle according to the present invention in contact with a nucleus.
Figure 34:
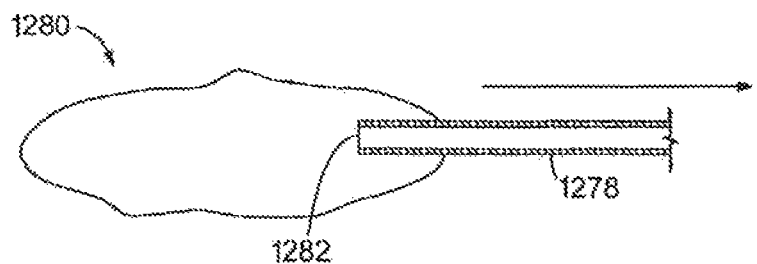
FIG. 34 is another partial lateral view of the present invention shown in FIG. 33.

Referring now to FIGS. 33 and 34 the numeral 1278 identifies a phacoemulsification needle constructed and moved in accordance with the invention described above. FIG. 33 illustrates a straight, unflared needle 1278 as it is being moved in the forward direction during longitudinal motion, showing the tip embedded in nucleus 1280 with the tip mouth 1282 in contact with nucleus 1280. FIG. 34 illustrates needle 1278 in a rearward direction during longitudinal phaco. As seen herein, tip mouth 1282 remains in contact with nucleus 1280. It is believed that the hybrid motion created by combining longitudinal motion of the needle with an off-axis needle or tip allow the aspiration suction to keep tip mouth 1282 in contact with nucleus 1280, greatly reducing repulsion, of the nucleus and making aspiration more efficient.

With repulsion reduced the surgeon spends less time "chasing" emulsified lens particles with the tip mouth in order to ultimately aspirate them. Reduced agitation of the gel helps to protect the eye and preserve the field of vision. Phacoemulsification is thus quieter, more efficient and less expensive for the surgeon.

Figure 35:
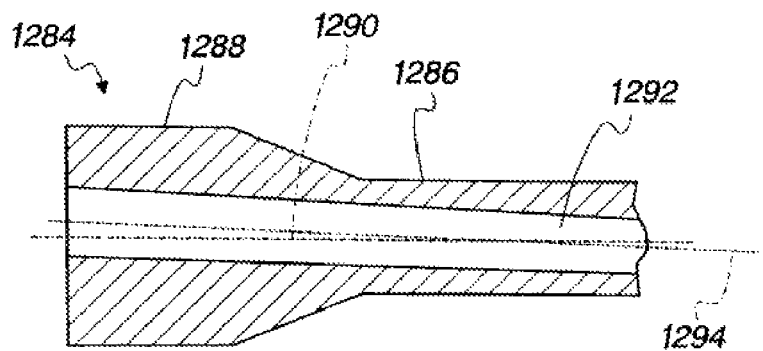
FIG. 35 is a partial sectional view of a phacoemulsification needle having an angled aspiration passageway and a symmetrical flared tip.

Referring now to FIG. 35, the numeral 1284 identifies a phacoemulsification needle having a needle body 1286 and a flared tip 1288. Needle body 1286 has a central axis 1290 extending therethrough. When the term "central axis" is used, it refers to an axis that is a locus of points about which the outer dimensions of the needle body are symmetrical. An aspiration passageway 1292 is formed through needle body 1286 and communicates with tip 1288. Aspiration passageway 1292 has a central axis 1294 extending therethrough, and as seen in FIG. 35, axes 1290 and 1294 meet at an angle and are not coincident, meaning that aspiration passageway 1292 is said to be angled with respect to needle body 1286.

Figure 36:
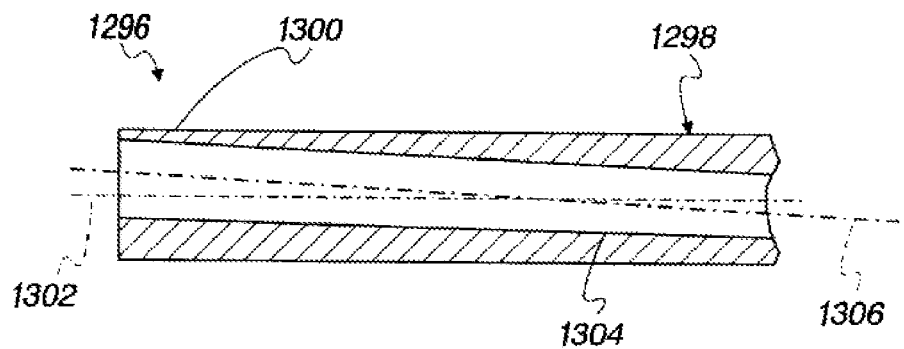
FIG. 36 is a partial sectional view of a phacoemulsification needle having an angled aspiration passageway and a non-flared tip.

Referring to FIG. 36, the numeral 1296 identifies phacoemulsification needle having a needle body 1298 which terminates at an unflared tip 1300. Needle body 1298 has a needle body axis 1302 extending centrally therethrough. An aspiration passageway 1304 is formed at an angle within needle body 1298 and extending through tip 1300 with aspiration passageway axis 1306 meeting axis 1302 at an angle.

Figure 37:
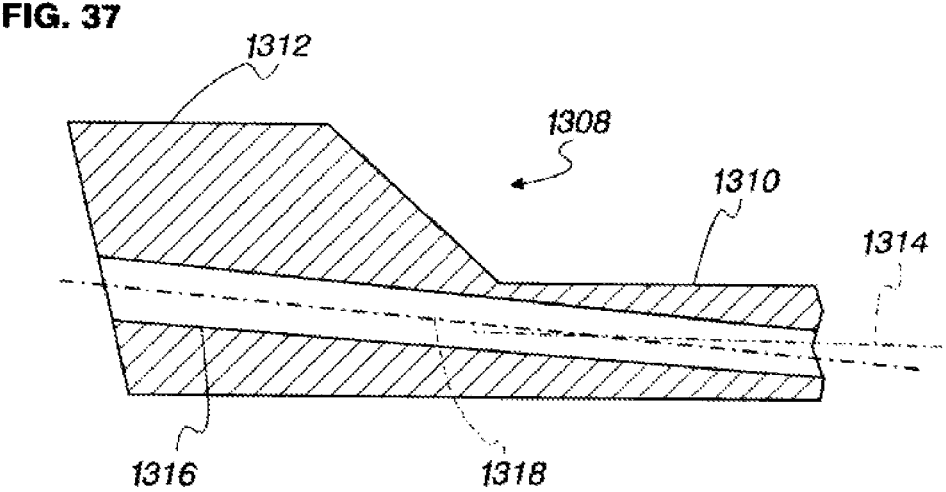
FIG. 37 is a partial sectional view of a phacoemulsification needle having an angled aspiration passageway and an asymmetrical flared tip.

Referring now to FIG. 37, the numeral 1308 identifies a phacoemulsification needle having a needle body 1310 terminating at a flared, offset tip 1312. Needle body 1310 has a central axis 1314. An angled aspiration passageway 1316 is formed through needle body 1310 and terminates at tip 1312. Aspiration passageway 1316 has a central axis 1318 of which meets axis 1314 at an angle.

In this embodiment, the "wobble" effect is produced by both the angled aspiration passageway 1316 and the offset tip 1312.

Figure 38:
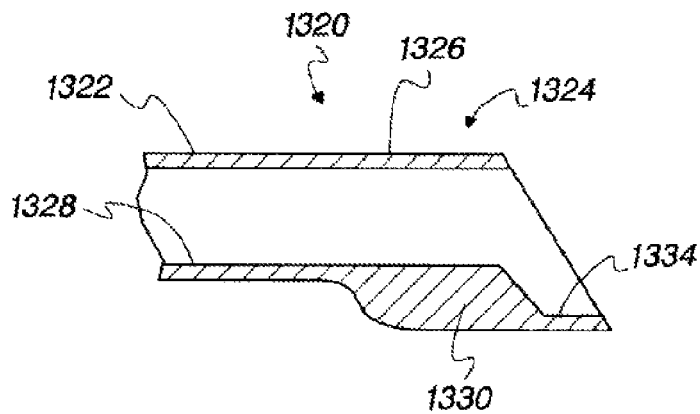
FIG. 38 is a partial sectional view of a flared asymmetrical phaco tip.
Figure 39:
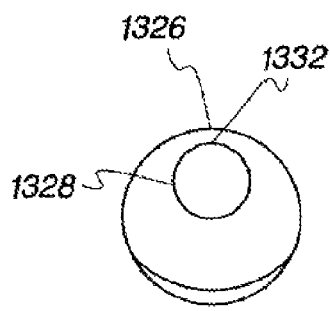
FIG. 39 is an end view of the tip of FIG. 38.

Referring now to FIG. 38, the numeral 1320 identifies a phacoemulsification needle having a needle body 1322 and a flared asymmetrical tip 1324. Tip 1324 has an outer wall 1326 and an inner wall 1328 as seen in FIG. 39, the distance between outer wall 1326 and inner wall 1328 varies about the inner circumference of tip 1324. In this embodiment, lower wall portion 1330 is at a maximum thickness and tapers upwardly so that wall portion 1332 positioned 180 degrees from lower wall portion 1330 is at a minimum thickness.

As further seen in FIG. 38, a land or offset 1334 is also formed with a tip 1320 creating another area of non-uniform distribution of tip mass.

Figure 40:
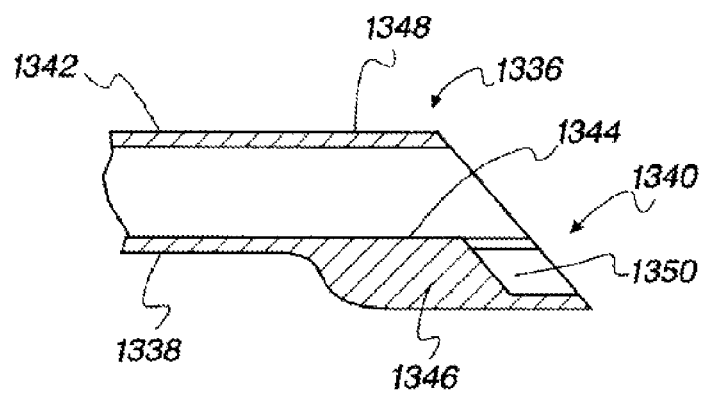
FIG. 40 is a partial sectional view of another embodiment of an asymmetrical needle tip.

Referring now to FIG. 40, the numeral 1336 having a needle body 1338 and a flared asymmetric tip 1340. As described in connection with FIG. 38, tip 1340 has an outer wall 1342 and an inner wall 1344, and the distance between inner and outer wall 1342 and 1344 varies around the circumference of tip 1340. As seen in FIG. 40, the lowermost wall portion 1346 is greater in dimension than upper wall portion 1348.

Figure 41:
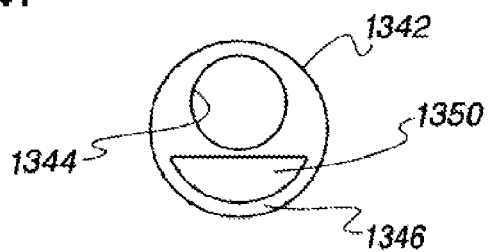
FIG. 41 is an end view of the needle of FIG. 40.

A lip cutout 1350 is formed in lower wall portion 1346 which, as seen in FIGS. 40 and 41 increases the non-uniform distribution of tip mass.

Figure 42:
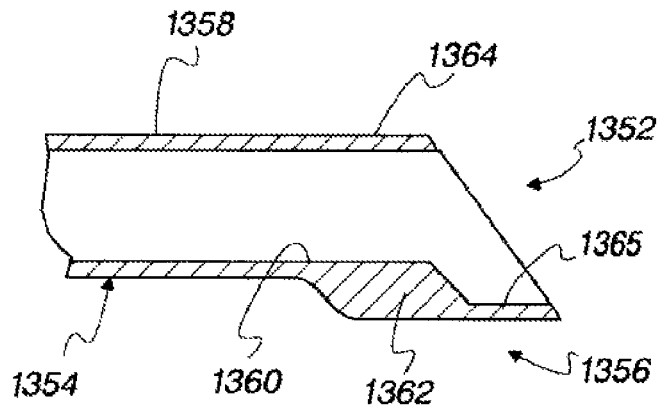
FIG. 42 is a partial sectional view of another embodiment of an asymmetrical needle tip.
Figure 43:
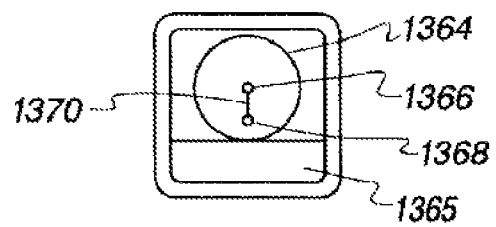
FIG. 43 is an end view of the tip of FIG. 42.

Referring to FIG. 42, the numeral 1352 identifies a phacoemulsification needle having a needle body 1354 and a flared asymmetrical tip 1356. As seen in FIG. 43, tip 1356 has a square cross sectional shape. Tip 1356 has an outer wall 1358 and an inner wall 1360 configured as described above in connection with FIGS. 38 and 40 to create a lower wall section 1362 of significantly greater thickness than upper wall portion 1364. A land or offset 1365 is formed in lower wall section 1362 which adds to the non-uniformity of the tip mass distribution. In this embodiment of the needle 152, there is an aspiration passage central axis 1366 that is offset from central tip axis 1368 by an offset distance 1370.

Figure 44:
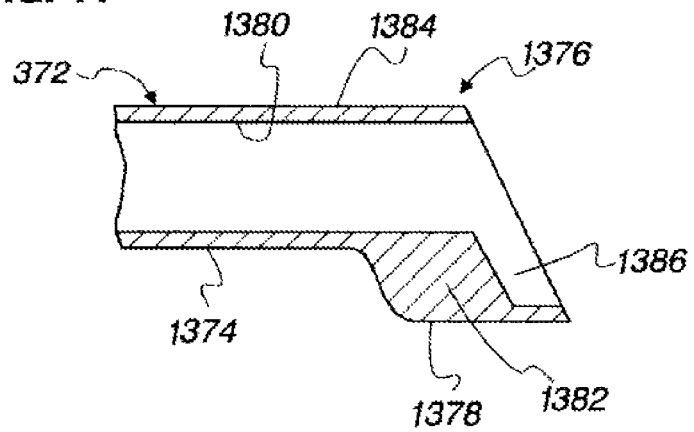
FIG. 44 is a partial sectional view of yet another embodiment of an asymmetrical needle tip.
Figure 45:
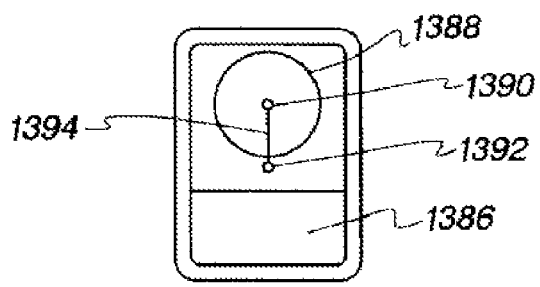
FIG. 45 is an end view of the tip of FIG. 44.

Referring now to FIG. 44, the numeral 1372 identifies a phacoemulsification needle having a body 1374 and a flared asymmetrical tip 1376. As described above, tip 1376 is formed with an outer wall 1378 and an inner wall 1380 to form a lower wall portion 1382 of significantly greater thickness than upper wall 1384. A land or offset 1386 is formed in lower wall portion 1382. As seen in FIG. 45, tip 1376 is rectangular in cross-sectional shape and in this embodiment, aspiration passageway 1388 has a central axis 1390 which is offset from central tip axis 1392 by an offset 1394. Referring now to FIG. 46, the numeral 1396 identifies a phacoemulsification needle having a needle body 1398 and a flared symmetrical tip 1400 formed with a front bevel 1402. As seen in FIG. 47, tip 1400 has a round cross-sectional shape.

As previously discussed, tip 1400 has a lower wall portion 1404 of significantly greater thickness than upper wall portion 1406 and a land or offset 1408 formed in lower wall portion 1404. As seen in FIG. 47, although tip 1400 is symmetrically shaped and centered on aspiration passageway 1410, it is still constructed with a non-uniform distribution of tip mass that provides the desired wobble effect.

Referring now to FIG. 48, the numeral 1412 identifies a phacoemulsification needle having a needle body 1414 and a flared tip 1416. As seen in FIG. 49, tip 1416 has a trapezoidal cross-sectional shape. As seen in FIG. 48, tip 1416 is formed with a lower wall portion 1418 that is substantially thicker than upper wall portion 1420. In the embodiment shown, as shown in FIG. 49, lower wall portion 1418 is of a substantially thicker construction while sidewall portions 1422, 1424 are substantially identical in thickness to upper wall portion 1420. In this embodiment, aspiration passageway 1426 has a central axis 1428 which is offset from central axis 1430 of tip 1416 by an offset distance 1432. An offset 1434 is formed in lower wall portion 1418 to create a more pronounced non-uniformity of tip mass distribution.

Figure 50:
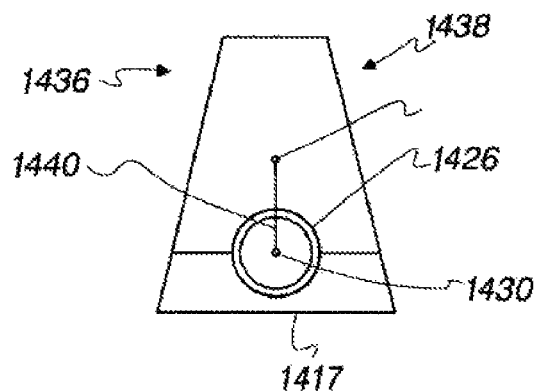
FIG. 50 is an end view f the tip of FIG. 48 showing the tip in a second selected offset.

Referring now to FIG. 50 the numeral 1436 identifies a phacoemulsification needle constructed in accordance with the above description for FIGS. 48 and 49. In this embodiment, tip 1438 is offset to place aspiration passage 1426 closer to lower wall portion 1418, creating an offset 1440.

Figure 51:
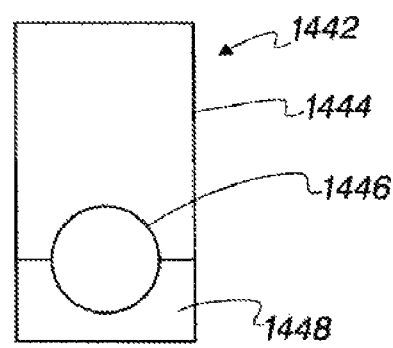
FIG. 51 is an end view of a rectangular tip showing a selected offset.

Referring now to FIG. 51, the numeral 1442 identifies a phacoemulsification needle having a rectangular tip constructed in accordance with the descriptions accompanying FIG. 45. In this embodiment, aspiration passageway 1446 is positioned closer to lower wall portion 1448 to produce an alternate offset to that shown in FIG. 45.

Figure 52:
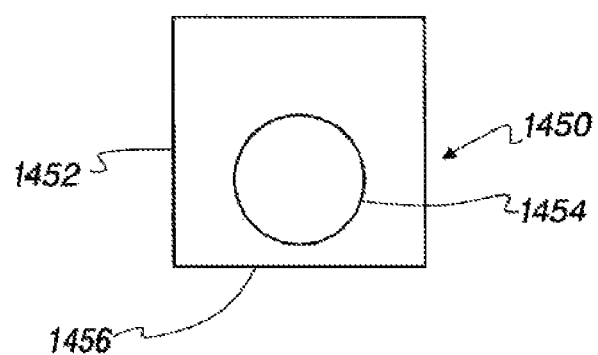
FIG. 52 is an end view of a square needle tip showing a selected offset.

Referring are now to FIG. 52, the numeral identifies a phacoemulsification needle having a tip 1452 with a square cross-section constructed in accordance with the descriptions accompanying FIG. 43. In this embodiment aspiration passageway 1454 is shown in an alternate position closer to lower wall portion 1456.

Figure 53:
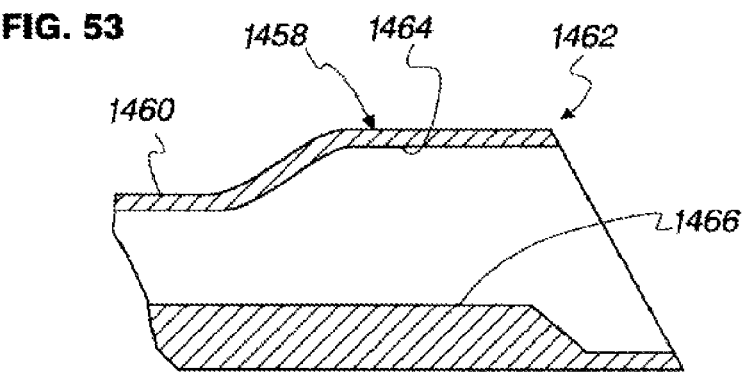
FIG. 53 is a partial sectional view of yet another embodiment of an asymmetric needle tip.
Figure 54:
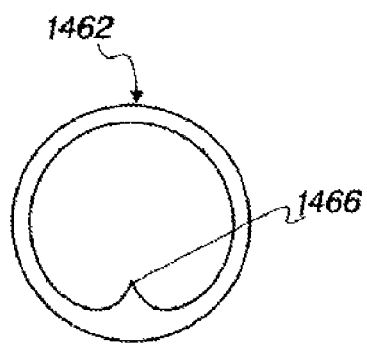
FIG. 54 is an end view of the tip of FIG. 53.

Referring now to FIG. 53, the numeral 1458 identifies a phacoemulsification needle having a needle body 1460 and a flared tip 1462. As seen in FIGS. 53 and 54, inner wall 1464 of tip 1462 is formed in a "scalloped" shape with a "peak" 1466 creating a somewhat upside-down apple-shaped cross-sectional shape, thus enhancing the non-uniform distribution of tip mass.

Figure 55:
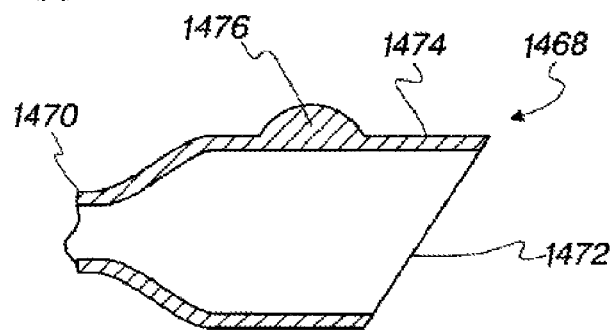
FIG. 55 is a partial lateral sectional view of a needle tip having a bump formed thereon.
Figure 56:
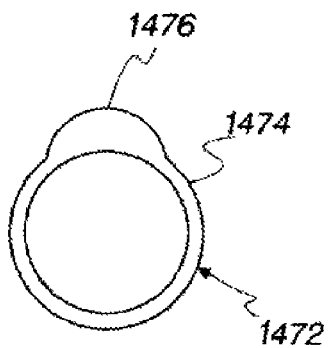
FIG. 56 is an end view of the tip of FIG. 55.

Referring now to FIG. 55, the numeral 1468 identifies a phacoemulsification needle having a needle body 1470 and a tip 1472, with an outer wall 1474. In this embodiment, non-uniform tip mass distribution is created by the formation of one or more protuberances, or "bumps" 1476 on outer wall 1474. FIG. 56 shows the positioning of a single bump 1476. If more than a single bump is formed, it is preferable that the pattern of bumps be on-symmetrical to maximize the wobble effect.

It should be understood that although the embodiments shown depict specific wall configurations the invention should not be so limited. Selected walls or wall portions of the phacoemulsification needle can be manufactured to various thicknesses to produce the non-uniform distribution of needle mass described herein.

Figure 57:
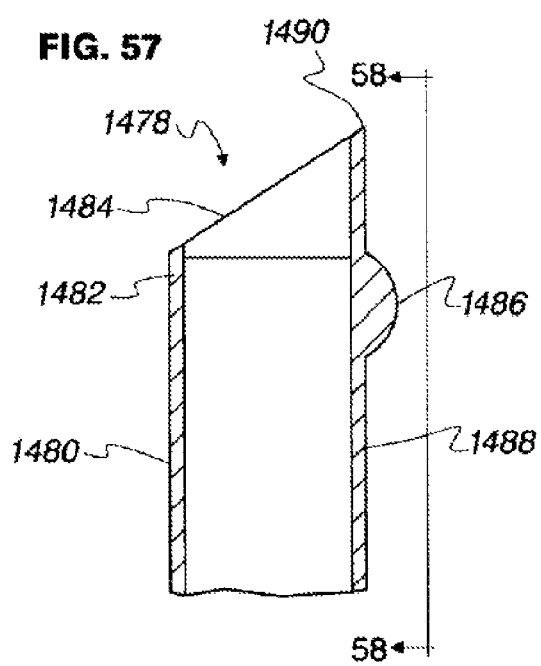
FIG. 57 is a partial sectional view or a bump formed on a non-flared needle tip.
Figure 58:
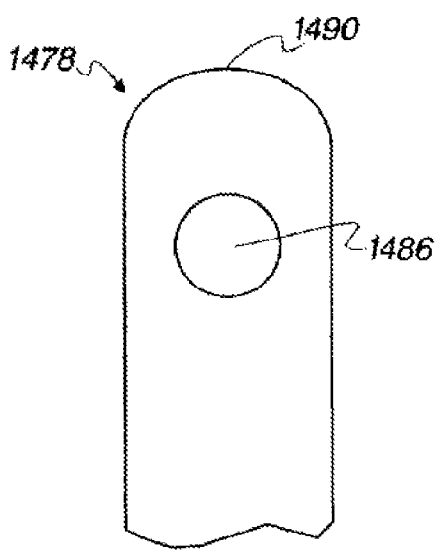
FIG. 58 is a view along line 58-58 of FIG. 57.

Referring now to FIG. 57, the numeral 1478 identifies a phacoemulsification needle having a needle body 1480 terminating in a non-flared tip 1482. In this embodiment, tip 1482 has a beveled lip 1484. As seen in FIG. 57, a bump 1486 is formed on tip 1482 on that portion of tip wall 1488 coextensive with the leading edge 1490 of beveled lip 1484. This same embodiment is shown in FIG. 58, although it should be understood that the placement of bump 1486 or others like it can be made in a number of different locations and configurations.

Figure 59:
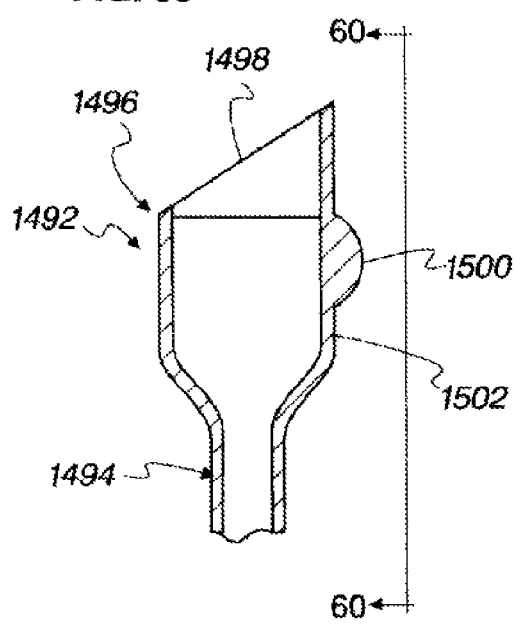
FIG. 59 is a partial lateral sectional view of a flared needle tip having a bump formed thereon.
Figure 60:
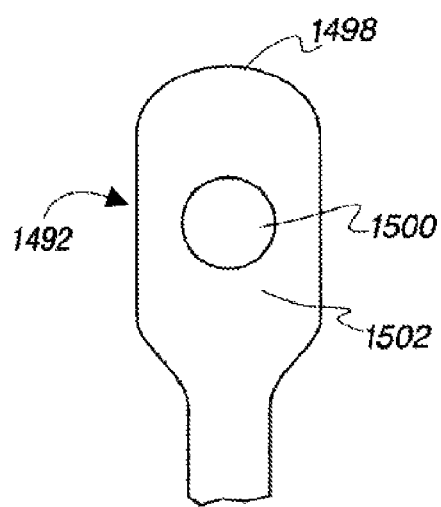
FIG. 60 is a view along 60-60 of FIG. 59.

Referring now to FIG. 59, the numeral 1492 identifies a phacoemulsification needle having a needle body 1494 and a flared, symmetrical needle tip 1496 having a beveled lip 1498. A bump 1500 is formed on outer tip wall 1502 as described above. Bump 1500 is also seen in FIG. 60.

Figure 61:
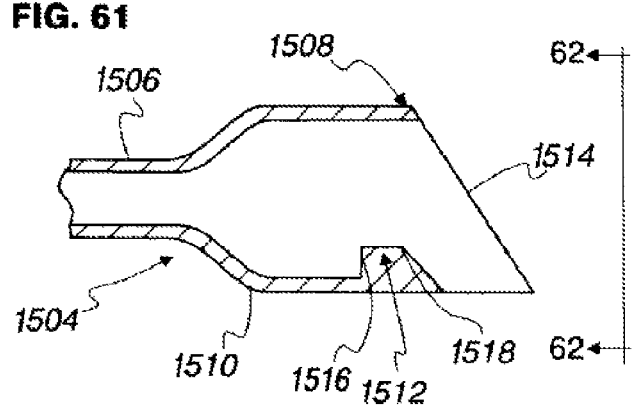
FIG. 61 is a partial lateral sectional view of a needle tip having an indentation formed thereon.
Figure 62:
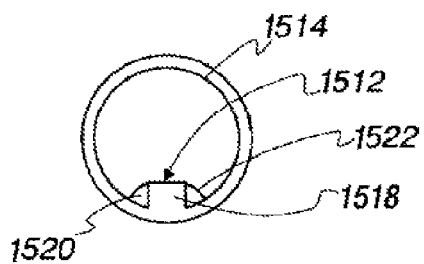
FIG. 62 a view along 62-62 of FIG. 61.

Creating tip mass non-uniformity can also be accomplished by forming inwardly-extending projections as well. Referring now to FIG. 61, the numeral 1504 identifies a phacoemulsification needle having a needle body 1506 and a flared tip 1508. Wall 1510 of tip 1508 has formed therein an inwardly-extending ridge portion 1512 proximate beveled lip 1514. As seen in FIGS. 61 and 62, ridge portion 1512 has an inwardly extending portion 1516, a depending portion 1518, and a pair of opposed side portions 1520 and 1522.

Figure 63:
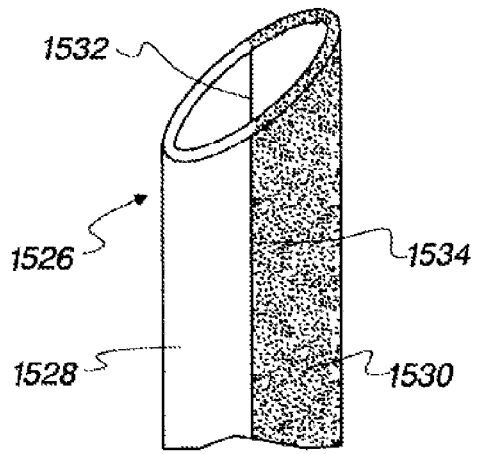
FIG. 63 is a partial elevational view of a composite unflared needle tip.

Non-uniform distribution of mass in a phaco tip can also be achieved while keeping a typical tip construction. Referring now to FIG. 63, the numeral 1526 identifies a phacoemulsification needle having tip wall segments 1528 and 1530, joined together at longitudinally-extending seams 1532 and 1534. In the embodiment shown, wall segment 1528 is formed from a material having a density differing from that of wall segment 1530. For example, well segment 1528 can be formed from gold, while segment 1530 can be formed from titanium. Even though a symmetrical needle design has been selected, the weights of segments 1528 and 1530 differ sufficiently to produce a wobble effect when needle 1526 is vibrated.

Figure 64:
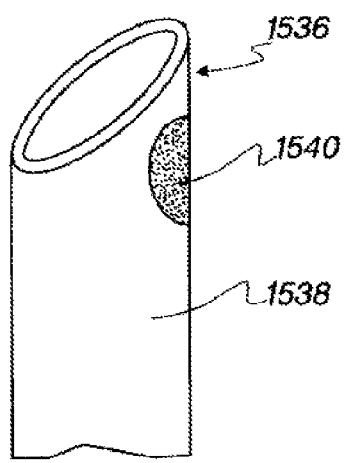
FIG. 64 is a partial elevational view a needle tip having a plug.
Figure 65:
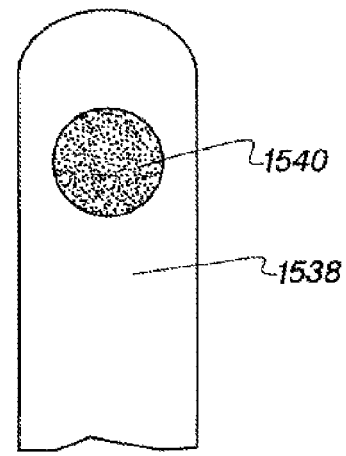
FIG. 65 is a partial elevational view of the needle of FIG. 64.

Referring now to FIGS. 64 and 65, then numeral 1536 identifies a phacoemulsification needle having an outer wall 1538 formed from a first selected material. A plug 1540, formed from is second material, is fit into a previously-formed aperture in wall 1538. The densities of said first and second materials differ sufficiently to produce a non-uniform material distribution of mass sufficient to produce a wobble effect when needle 1536 is vibrated.

Figure 66:
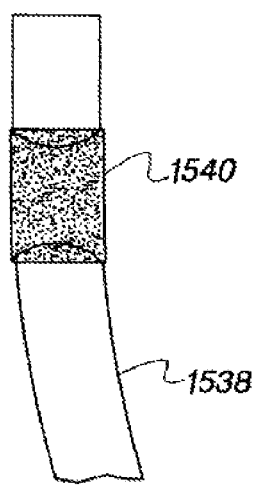
FIG. 66 is a partial sectional view of the tip wall of FIG. 65 showing the plug set therein.

FIG. 66 is a partial side sectional view showing the insertion of plug 1540 through wall 1538.

Figure 67:
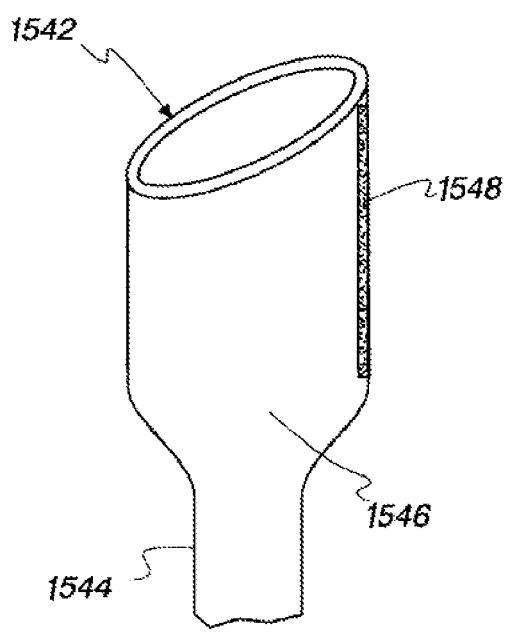
FIG. 67 is a partial elevational view of a flared composite tip.
Figure 68:
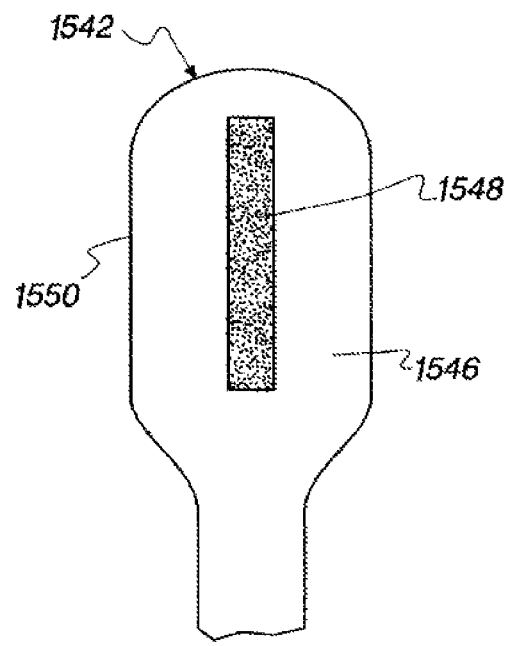
FIG. 68 is another partial elevational view of the tip of FIG. 67.

Referring now to FIGS. 67 and 68, the numeral 1542 identifies a phacoemulsification needle having a needle body 1544 and a flared tip 1546 formed from a first material. An insert strip 1548 formed from a second material is secured within a previously-formed slot in sidewall 1550 of tip 1546.

Needle body 1544 and insert strip 1548 are of sufficiently different densities to produce a non-uniform material distribution of mass sufficient to produce a wobble effect when needle 1546 is vibrated.

Figure 69:
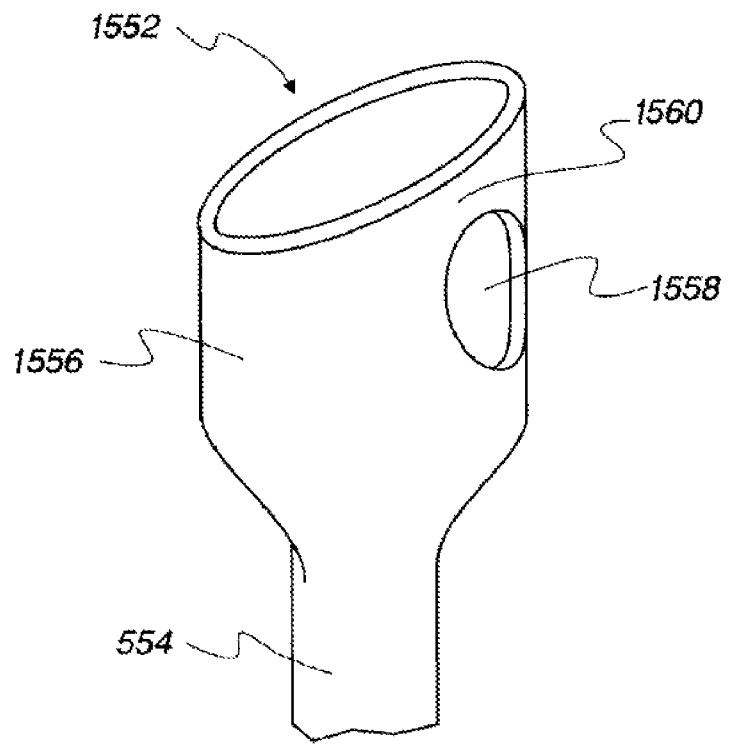
FIG. 69 is a partial elevational view showing an insert port formed on a flared needle tip.

Referring now to FIG. 69 the numeral 1552 identifies a phacoemulsification needle having a needle body 1554 and a needle tip 1556. An aperture 1558 is shown having been formed in sidewall 1560.

Figure 70:
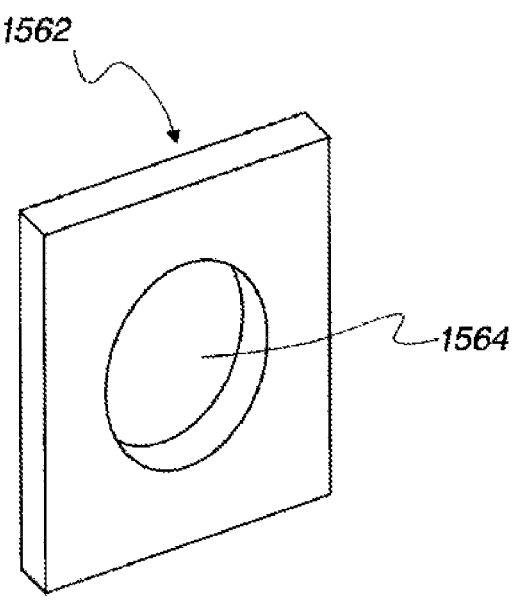
FIG. 70 is an enlarged portion of FIG. 69.

Referring now to FIG. 70 the numeral 1562 identifies a block of material with a different density than that of the material forming tip 1556. A plug 1564 is shown being punched out from block 1562, sized and shaped to be press-fit into aperture 1558 to form the tip described above with respect to FIGS. 64 and 65.

Although the plugs and strips described above have been shown to have specific shapes these shapes are exemplary only. Other shapes can be selected depending upon the desired geometry and operating characteristics of the needle being designed. Combinations of more than two desired materials can also be used.

Referring now to FIGS. 71 through 80, variations of phacoemulsification needles and tips are shown embodying the principles of the present invention by forming thereon non-uniform or skewed bevels and ridges to produce a desired wobble motion.

Figure 71:
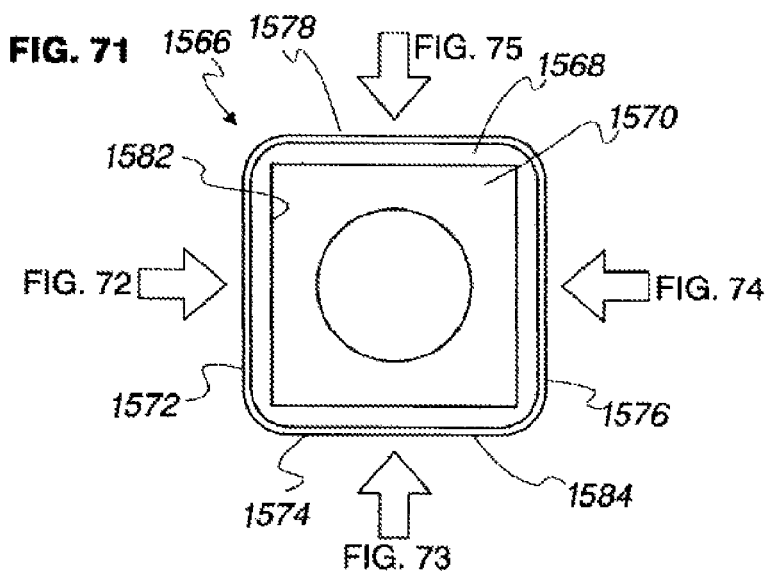
FIG. 71 is a top plan view of a tip having multiple skewed ridges and bevels.

Referring now to FIG. 71, the numeral 1566 identifies a phacoemulsification needle tip having a square cross-sectional shape with a lip 1568 defining a tip mouth 1570. Tip 1566 has a first side 1572, a second side 1574, a third side 1576, and a fourth side 1578.

Figure 72:
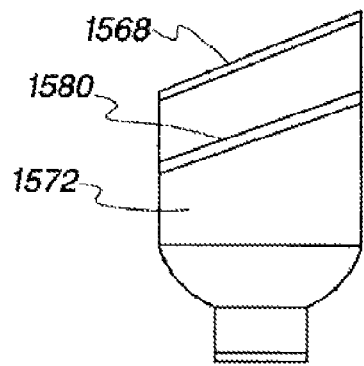
FIG. 72 is a view taken at a of FIG. 71.

In FIG. 72, side 1572 is shown. As seen in FIG. 72, lip 1568 is beveled so that viewed from direction a it appears to be slanted. A skewed ridge 1580 is formed on side 1572 and can be formed either on interior surface 1582 or outer surface 1584 of tip 1566.

Figure 73:
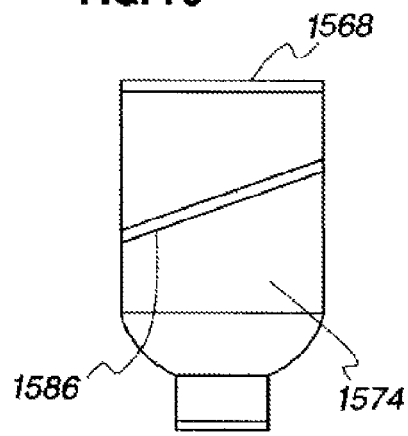
FIG. 73 is a view taken at b of FIG. 71.

Referring now to FIG. 73, side 1574 is shown, with lip 1568 seen as extending straight across. Ridge 1586 extends across either interior surface 582 or outer surface 1584.

Figure 74:
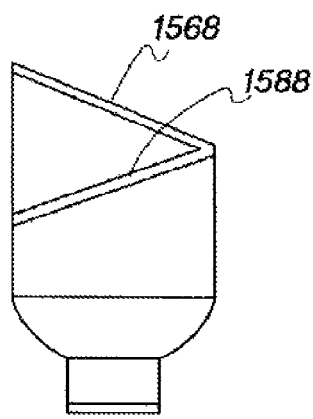
FIG. 74 is a view taken at e of FIG. 71.

Referring now to FIG. 74, side 1576 is shown, with lip 1568 seen as sloping downward from left to right. Ridge 1588 extends across either interior surface 1582 or outer surface 1584.

Figure 75:
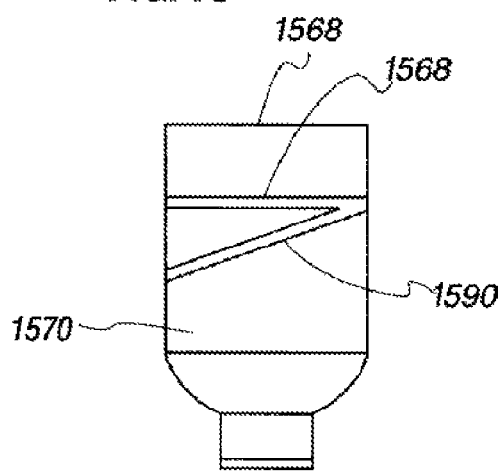
FIG. 75 is a view taken at d of FIG. 71.

Referring now to FIG. 75, is shown, with lip 1568 seen as extending straight across. Ridge 1590 extends across either interior surface 1582 or outer surface 1584.

Referring now to FIG. 76, the numeral 1592 identifies a phacoemulsification needle having a round cross-sectional shape having exterior wall segments 1594, 1596, 1598, and 1600. For purposes of this description we shall assume that each wall segment is one-fourth of the total circumference of needle 1592.

Outer and inner sidewalls 1602 and 1604, define a lip 1606 which, in turn, defines a tip mouth 1608.

In FIG. 77, side portion 1594 is shown. As seen in FIG. 77, lip 1606 is beveled so that viewed from direction a it appears to be slanted. A skewed ridge 1610 is formed on side portion and can be formed either on interior wall 1602 or exterior wall 1604 of needle 1592.

Referring now to FIG. 78, side portion 1596 is shown, with lip 1606 seen as curving straight across. Skewed ridge 1612 can be formed either on interior wall 1602 or exterior well 1604 of needle 1592.

Referring now to FIG. 79, side portion 1598 is shown, with lip 1606 shown as sloping downward from left to right. Skewed ridge 1614 can be formed either on interior wall 1602 or exterior wall 1604 of needle 1592.

Referring now to FIG. 80, side portion 1600 is shown, with lip 1606 seen as curving from left to right. Skewed ridge 1616 can be formed either on interior well 1602 or exterior wall 1604 of needle 1592.

Figure 81:
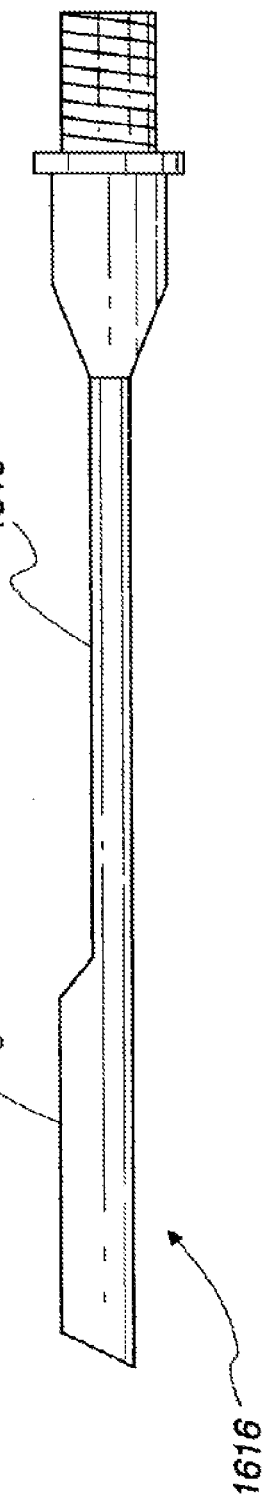
FIG. 81 is a lateral elevation of a phacoemulsification needle having an asymmetric needle body.
Figure 82:
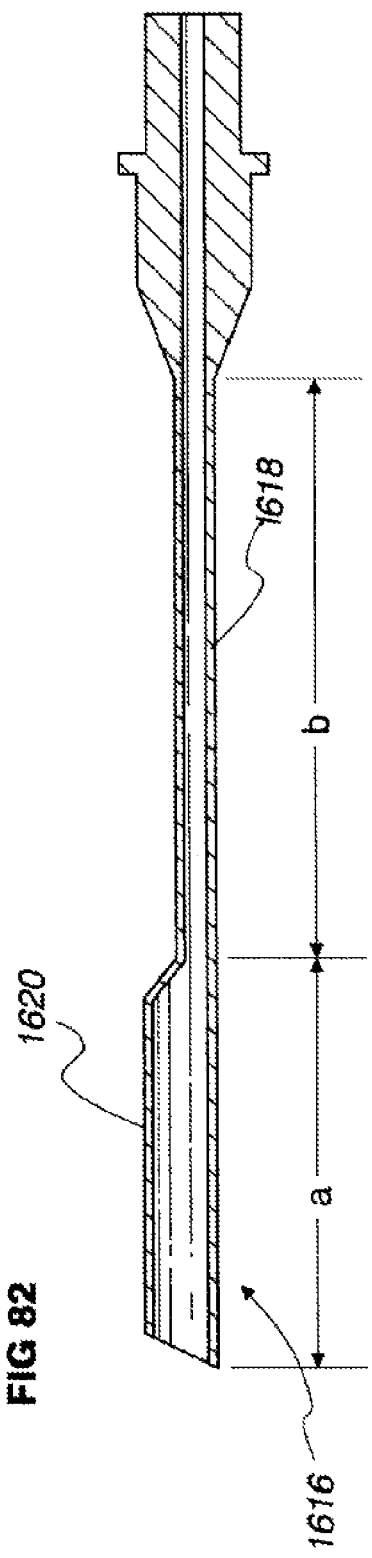
FIG. 82 is a sectional view of the needle of FIG. 81.

Referring now to FIG. 81 the numeral 1616 identifies a phacoemulsification needle having a needle body 1618 and an extended asymmetric tip 1620. Lengthening tip 1620 created a longitudinal non-uniformity of needle mass as well as the non-uniformity inherent in the asymmetric configuration of tip 1620. As seen in FIG. 82, it is the ratio of distance "a" (the effective length of tip 1620) to the distance "b" (the effective length of needle body 1618) that will determine the extent of the wobble motion imparted to needle 1616.

Referring now to FIG. 83 the numeral 1622 identifies a phacoemulsification needle having a needle body 1624 and an extended needle tip 1626. In the embodiment shown needle tip 1626 is symmetrical, yet it is expected that the extended length of tip 1626 will produce a wobble motion when needle 1622 is vibrated. Referring now to FIG. 84 it is the ratio of distance "a" the effective length of tip 1626) to the distance "b" (the effective length of needle body 1624) that will determine the extent of the wobble motion imparted to needle 1622.

Figure 85:
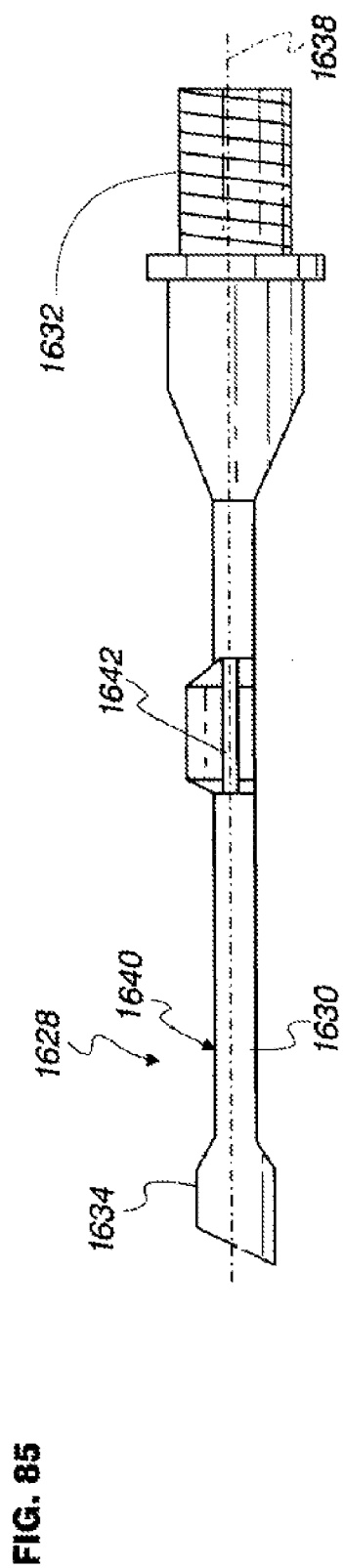
FIG. 85 is a lateral elevation of a phacoemulsification needle having an asymmetrical weight affixed to the needle body portion.
Figure 86:
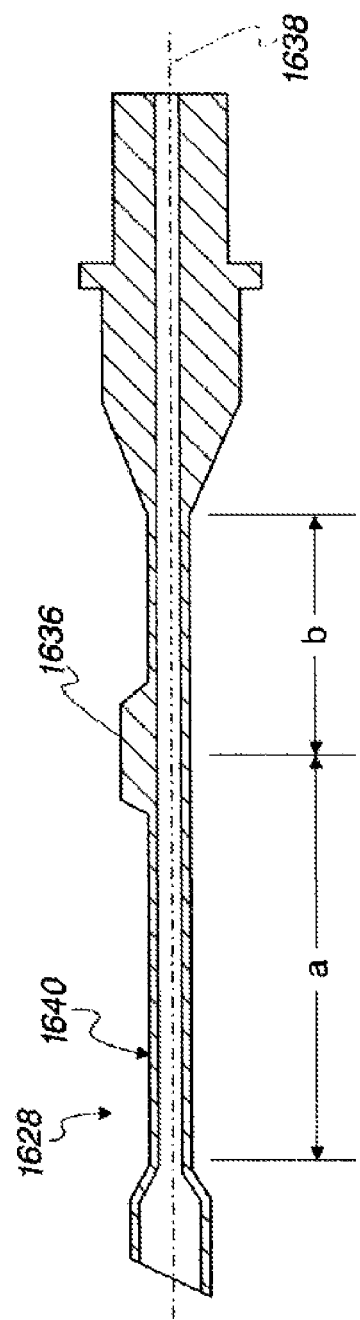
FIG. 86 is a sectional view of the needle of FIG. 85.

Referring now to FIG. 85 and FIG. 86, the numeral 1628 identifies a phacoemulsification needle having a needle body 1630 with a needle mount 1632 at its proximal end and a needle tip 1634 at its distal end. A wobble motion is imparted by the attachment of an asymmetrical weight 1636 on needle body 1630 intermediate mount 1632 and tip 1634 and the vibration of needle 1628 by a selected handpiece. In the embodiment shown, weight 1636 is asymmetrical relative to needle body 1630, meaning that the distribution of the mass of weight 1636 is non-uniform about the needle body axis 1638.

As seen in both FIGS. 85 and 86, at least a portion of weight 1636 extends outward from the outer surface 1640 of needle body 1630. One or more grooves 1642 may be formed in weight 1636 to act as channels for the flow of irrigating liquid through an irrigation sleeve (not shown) mounted to needle 1628.

Weight 1636 may be integrally formed with needle body 1630 or may be attached thereto. If attached, weight 1636 may be formed from material having a different density than that used to form needle 1628, adding to the wobble effect.

As seen in FIG. 86, the placement of weight 1636 along needle body 1630 may be varied, with the distances "a" and "b" selected to create a desired amount and character of wobble.

Referring now to FIG. 87, the numeral 1644 identifies a phacoemulsification needle having a needle body 1646 with a needle mount 1648 at its proximal end and a needle tip 1650 at its distal end. A wobble motion is imparted by the attachment of a symmetrical weight 1652 on needle body 1646 intermediate mount 1648 and tip 1650 and the vibration of needle 1644 by a selected handpiece. In the embodiment shown, weight 1652 is symmetrical relative to needle body 1646, meaning that the distribution of the mass of weight 1652 is uniform about the needle body axis 1654. In this embodiment it is the non-uniformity of mass along axis 1654 that creates the wobble effect.

As seen in both FIGS. 87 and 88, at least a portion of weight 1652 extends outward from the outer surface 1656 of needle body 1646. One or more grooves 1658 may be formed in weight 1652 to act as channels for the flow of irrigating liquid through an irrigation sleeve (not shown) mounted to needle 1644.

Weight 1652 may be integrally formed with needle body 1646 or may be attached thereto. If attached, weight 1652 may be formed from material having a different density than that used to form a needle 1644, adding to the wobble effect.

As seen in FIG. 88, the placement of weight 1652 along needle body 1646 may be varied, with the distances "a" and "b" selected to create a desired amount and character of wobble.

While weights 1636 and 1652 are shown in a selected position it is a feature of the present invention that such weights can be moved along the needle body to adjust the character of the wobble. For example, as seen in FIGS. 87 and 88, a series of grooves or detents can be formed along needle body 1646. As seen in FIG. 88, a corresponding ring or peg 1662 can be formed on weight 1652 positioned and sized to register with selected of said detents, such as detent 1664. Other methods of positioning and securing weight 1652 along needle body 1646 can also be used. Weight 1652 can then be positioned as desired along needle body 1646 to adjust the vibrational characteristics of the needle.

While the embodiments illustrate weights 1636 and 1652 in a selected shape, it should be understood that said weights can be formed in a variety of cross-sectional and longitudinal configurations, such as square, triangular, oval and irregular shapes as well.

It is also contemplated that the surfaces of weights 1636 and 1652 may be fluted to provide flow paths for the irrigating liquid.

Another embodiment of the present invention creates the wobble effect by putting one or more twists into the phacoemulsification needle tip creating a somewhat fluted configuration.

Figure 89:
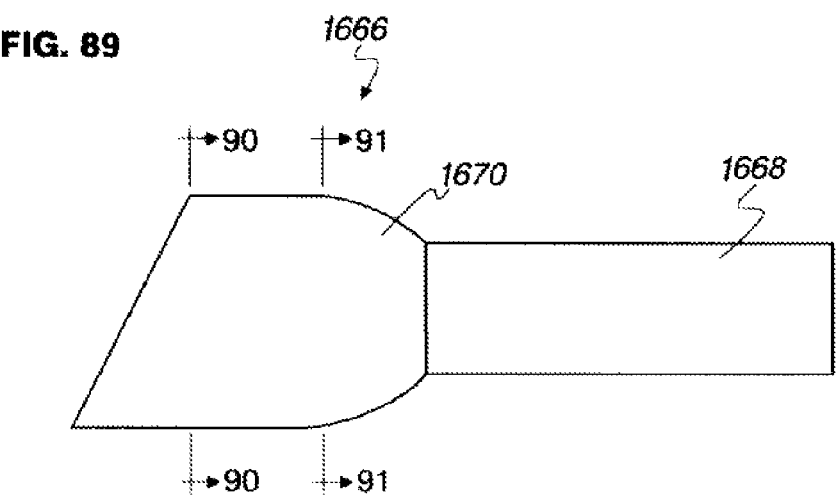
FIG. 89 is a lateral view of portion of a phacoemulsification needle having a twisted tip.

Referring now to FIG. 89, the numeral 1666 identifies a port of a phacoemulsification needle having a needle body 1668 and a flared needle tip 1670. For the purposes of this description, tip 1670 is illustrated as having a square cross-section. During the manufacturing process, tip 1670 is twisted such that the section identified at 90-90 of FIG. 89 is turned to a position approximately 90 degrees from that of the section identified by 91-91 of FIG. 89.

Figure 90:
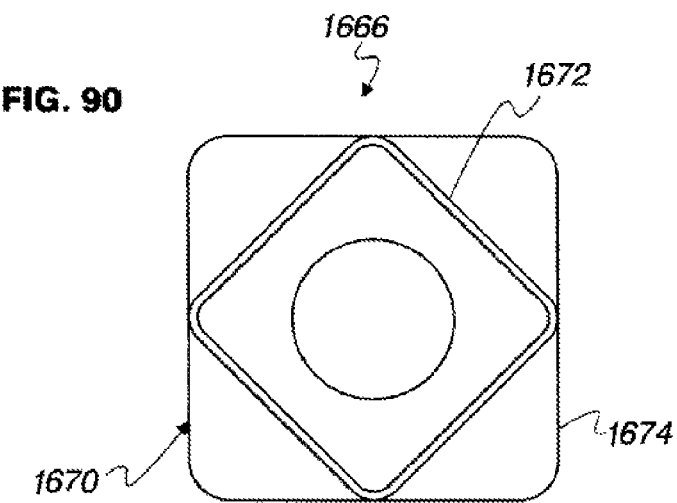
FIG. 90 is a view along 90-90 of FIG. 89.

Referring to FIG. 90, tip 1670 is viewed from 90-90 of FIG. 89 showing that the first section 1672 of tip 1666 is rotated approximately 90 degrees with reference to rearmost section 1674.

Figure 91:
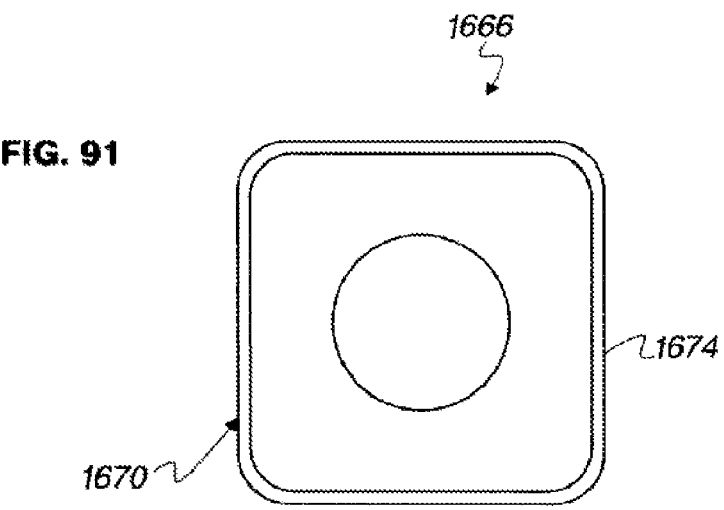
FIG. 91 is a view along 91-91 of FIG. 89.

Referring now to FIG. 91, the tip 1670 is viewed from 91-91 of FIG. 89 showing that the remaining portion of tip 1670 is not twisted.

While the foregoing examples have used a flared tip with a square cross-section and a single twist, it contemplated that other cross-sectional shapes can be used as well and it is also contemplated that the number of twists can be varied, as can be the rotation or each twist. For example, in the example shown in FIG. 89, first section 1672 may have been twisted to an angle of 30 degrees with respect to rearmost section 1674. The twisting of tip 1670 creates an additional irregularity in the shape of needle 1666 adding to the wobble effect.

The foregoing has described various embodiments of the present invention as they relate to non-uniform distribution of mass in constructing a phacoemulsification needle. It is expected that these embodiments can be combined to add efficacy to a needle design. For example, the skewed ridges of FIGS. 71-80 can be added to the various tip designs described herein. Plugs of differing material can be added to the designs shown herein, as described in connection with FIGS. 63-70, as well as bumps as described in connection with FIGS. 55-60. Angled aspiration passageways such as described in connection with FIGS. 35-37.

The foregoing variations are expected to be effective with handpieces producing longitudinal, torsional, elliptical or other eccentric motions and are expected to demonstrate increased efficiency during the phacoemulsification process.

Thus, needles embodying the present invention create a hybrid motion in dependent of the type of handpiece and control console used. For those instruments designed to create a torsional vibratory motion, needles embodying the present invention create tip motion having a wider cutting range, covering more area. As observed, this hybrid motion appears to exhibit an energy focused more at the tip of the needle surface area, reducing wasted energy. The increase in efficiency exhibited by needles embodying the present invention has been demonstrated by comparing the cumulative dissipated energy levels for a handpiece using both the current and conventional needles to perform the same procedure. Use of the needles disclosed herein results in significantly reduced chatter, repulsion and thermal damage.

It is expected that the principles described herein can also be applied to other surgical instruments as well, such as those used for liposuction and coronary plaque removal. While the present invention has been described in the context of cataract removal, it should be understood that the principles of the present invention can be applied to the removal of different types of tissue as well such as tumors and the like.

The foregoing disclosure of specific embodiments is intended to be illustrative of the broad concepts comprehended by the invention.

What is claimed is:

1. A phacoemulsification needle for use with a phacoemulsification handpiece, said needle comprising:
    an elongate needle body having an outer surface, an inner surface, a proximal end and a distal end,
        said elongated needle body defining a central longitudinal needle axis,
        said elongated needle body having an axial length along said central longitudinal needle axis between said proximal and distal ends,
        said elongated needle body having an aspiration passageway extending through said elongated needle body,
        said elongated needle body inner and outer surfaces defining therebetween a needle body wall having a body wall thickness;
    a flaring needle tip formed at said elongated needle body distal end,
        said flaring needle tip having an exterior surface and an interior surface defining therebetween a needle tip wall terminating at a lip on a distal end of the flaring needle tip,
        said flaring needle tip having a mouth defined by said lip, said mouth defining a central longitudinal axis, said mouth central longitudinal axis substantially parallel to and offset from said elongated needle body central longitudinal needle axis, and
        at least a portion of said needle tip wall having a non-uniform distribution of mass.

2. The phacoemulsification needle as recited in claim 1 wherein said non-uniform distribution of mass comprises a thickened portion of said needle tip wall that is thicker than a remaining portion of said needle tip wall.

3. The phacoemulsification needle as recited in claim 2 wherein said remaining portion of said needle tip wall has a thickness that is substantially equal to said body wall thickness.

4. The phacoemulsification needle as recited in claim 2 wherein said thickened portion of said needle tip wall has a cavity formed therein.

5. The phacoemulsification needle as recited in claim 2 wherein said thickened portion of said needle tip wall is non-uniform in thickness.

6. The phacoemulsification needle as recited in claim 5 wherein said non-uniform thickened portion of said needle tip wall has a scalloped cross-sectional shape when viewed in a plane perpendicular to said mouth central longitudinal axis.

7. The phacoemulsification needle as recited in claim 2 wherein said thickened portion of said needle tip wall comprises at least one protuberance extending outward from said tip exterior surface.

8. The phacoemulsification needle as recited in claim 2 wherein said thickened portion comprises at least one internal ridge, said at least one internal ridge formed on said tip interior surface and extending in a direction toward said mouth central longitudinal axis.

9. The phacoemulsification needle as recited in claim 1 wherein said non-uniform distribution of mass comprises a weighted segment of said needle tip wall formed from a material having a density different than that of the density of a material forming a remaining portion of said needle tip wall.

10. The phacoemulsification needle as recited in claim 9 wherein said weighted segment comprises a plug; said needle tip wall having an opening formed therein sized and shaped to fit and hold said plug, said plug having a density different than that of said needle tip wall.

11. The phacoemulsification needle as recited in claim 9 wherein said flaring needle tip is formed from at least first and second tip segments joined together to form said flaring needle tip; at least one said tip segment formed from a material with a density different than that of the remaining tip segment or segments.

12. The phacoemulsification needle as recited in claim 1 in combination with a phacoemulsification handpiece, said phacoemulsification handpiece for being coupled to said phacoemulsification needle to cause said flaring needle tip to move eccentrically when said elongated needle body is vibrated at ultrasonic frequencies.

* * * * *